United States Patent
Woerz et al.

(10) Patent No.: US 9,458,080 B2
(45) Date of Patent: Oct. 4, 2016

(54) PROCESS FOR OBTAINING ACRYLIC ACID

(71) Applicant: BASF SE, Ludwigshafen am Rhein (DE)

(72) Inventors: Nicolai Tonio Woerz, Darmstadt (DE); Lukas Schulz, Mannheim (DE); Tim Blaschke, Stuttgart (DE); Marco Hartmann, Jockgrim (DE); Feely Ruether, Frankenthal (DE); Yan Li, Mannheim (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 14/958,207

(22) Filed: Dec. 3, 2015

(65) Prior Publication Data

US 2016/0159724 A1 Jun. 9, 2016

Related U.S. Application Data

(60) Provisional application No. 62/086,753, filed on Dec. 3, 2014.

(30) Foreign Application Priority Data

Dec. 3, 2014 (DE) .................. 10 2014 017 815

(51) Int. Cl.
| | |
|---|---|
| C07C 51/43 | (2006.01) |
| C07C 57/04 | (2006.01) |
| C07C 67/343 | (2006.01) |
| C07C 51/47 | (2006.01) |

(52) U.S. Cl.
CPC .............. *C07C 51/47* (2013.01); *C07C 51/43* (2013.01); *C07C 57/04* (2013.01); *C07C 67/343* (2013.01)

(58) Field of Classification Search
CPC ............................ C07C 51/43; C07C 51/353
See application file for complete search history.

(56) References Cited

U.S. PATENT DOCUMENTS

| | | | |
|---|---|---|---|
| 2013/0085302 A1* | 4/2013 | Kotsianis et al. | ...... C07C 51/42 562/600 |
| 2014/0121403 A1 | 5/2014 | Nagaki et al. | |

FOREIGN PATENT DOCUMENTS

WO     WO 2014/070735 A1     5/2014

OTHER PUBLICATIONS

International Search Report issued Feb. 11, 2016 in PCT/EP2015/078500 (with English Translation of Categories of Documents).
James F. Vitcha et al., "Vapor Phase Aldol Reaction", Acrylic Acid by the Reaction of Acetic Acid and Formaldehyde, I & EC Product Research and Development, vol. 5, No. 1, Mar. 1966, pp. 50-53.

* cited by examiner

*Primary Examiner* — Paul A Zucker
(74) *Attorney, Agent, or Firm* — Oblon, McClelland, Maier & Neustadt, L.L.P.

(57) ABSTRACT

A process for obtaining acrylic acid, comprising (a) providing a liquid stream S7 comprising acetic acid and acrylic acid, where the molar ratio of acetic acid to acrylic acid in stream S7 is greater than 1:1, (b-1) crystallizing a portion of the acetic acid present in stream S7 to obtain solid crystallized acetic acid in its mother liquor, (b-2) separating the mother liquor from the acetic acid crystallized in (b-1) to obtain the solid crystallized acetic acid and a liquid stream S8 comprising acrylic acid and acetic acid, (c) separating stream S8 into at least one stream S10 depleted of acrylic acid compared to S8 and a stream S11 enriched in acrylic acid compared to S8.

16 Claims, 1 Drawing Sheet

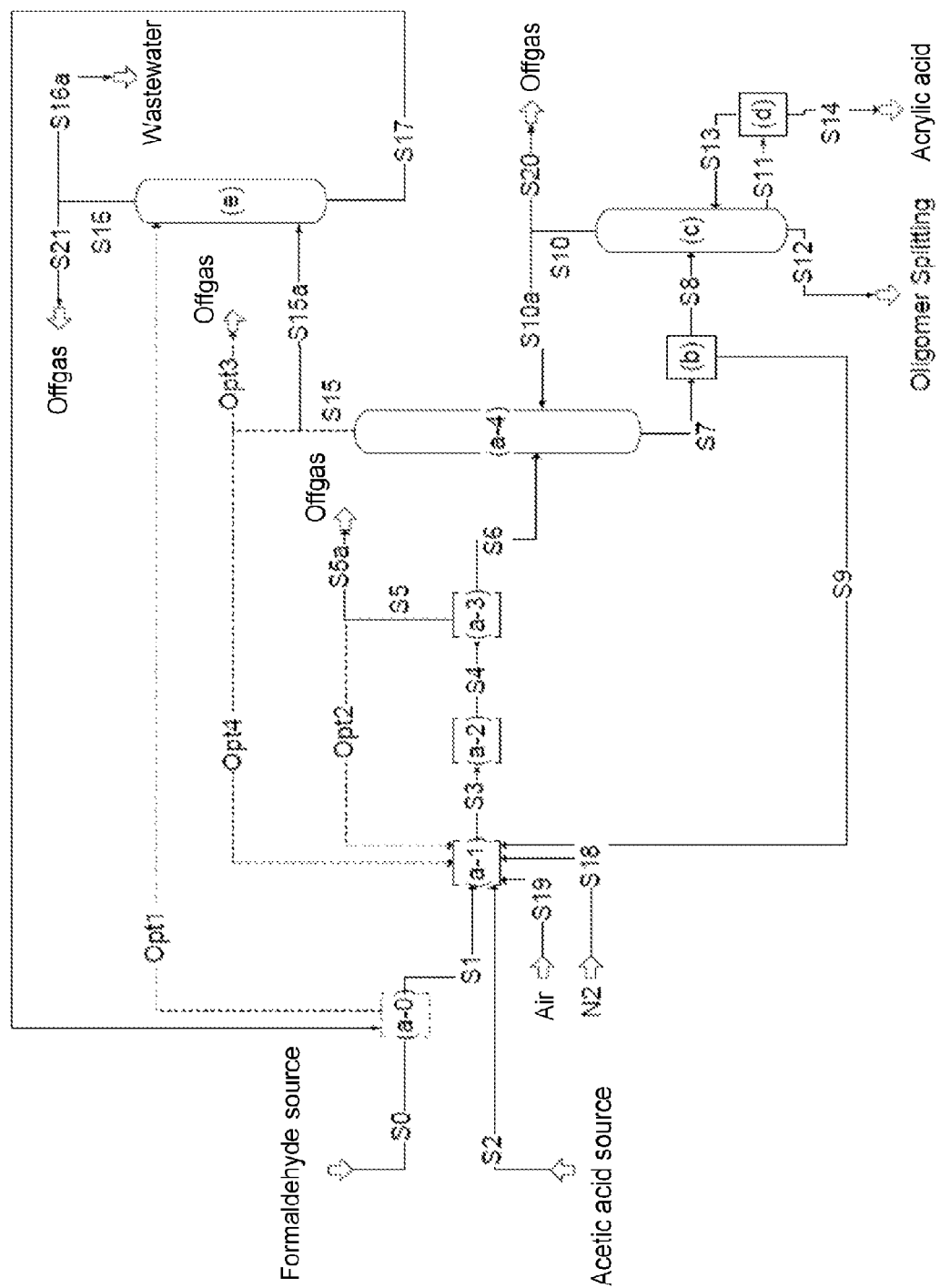

PROCESS FOR OBTAINING ACRYLIC ACID

The present invention relates to a process for obtaining acrylic acid, which comprises the providing of a liquid stream S7 comprising acetic acid and acrylic acid, where the molar ratio of acetic acid to acrylic acid in stream S7 is greater than 1:1. The process further comprises the crystallizing of a portion of the acetic acid present in stream S7 to obtain solid crystallized acetic acid in its mother liquor, the separating of the mother liquor from the crystallized acetic acid to obtain the solid crystallized acetic acid and a liquid stream S8 comprising acrylic acid and acetic acid, and the separating of stream S8 into at least one stream S10 depleted of acrylic acid compared to S8 and a stream S11 enriched in acrylic acid compared to S8.

U.S. Provisional Patent Application No. 62/086,753, filed 3 Dec. 2014, is incorporated into the present application by literature reference. With regard to the abovementioned teachings, numerous changes and deviations from the present invention are possible. It can therefore be assumed that the invention, within the scope of the appended claims, can be performed differently from the way described specifically herein.

Acrylic acid, an important monomer for production of homo- and copolymers, is typically obtained by a heterogeneously catalyzed two-stage partial oxidation proceeding from propene, with acrolein as intermediate.

As an alternative, Vitcha and Sims, I & EC Product Research and Development, Vol. 5, No. 1, March 1966, pages 50 to 53, describe the synthesis of acrylic acid in a gas phase reaction proceeding from acetic acid and formaldehyde in a molar ratio of 10:1. While the excess of acetic acid leads to a higher yield of acrylic acid, this simultaneously results in an incomplete acetic acid conversion. In order to be able to conduct such a process in an economically viable manner, it is necessary to recycle the unconverted acetic acid into the process, which entails an appropriate workup of the unconverted acetic acid.

WO 2014/070735 A1 describes a process for preparing acrylic acid from formaldehyde and acetic acid in an aldol condensation, where the molar ratio of acetic acid to formaldehyde is greater than 1 and may be up to 10. There are descriptions of various variants for workup of the product stream which allow recycling of unconverted acetic acid, for example the distillative separation of the crude product stream into an acetic acid-rich stream and an acrylic acid-rich stream, and adsorptive methods with an organic solvent or water.

One of the problems addressed by the present invention was therefore that of providing an advantageous process for obtaining acrylic acid, especially proceeding from acetic acid and formaldehyde, comprising the recycling of unconverted acetic acid. More particularly, one of the problems addressed by the present invention was that of providing a simplified process in which no column T—as obligatory in WO 2014/070735 A1—has to be used for removal of an acetic acid-rich stream to obtain an acrylic acid-rich stream.

It has been found that, surprisingly, such a process can be provided by virtue of unconverted acetic acid present in an acrylic acid-comprising product stream which results from the obtaining of acrylic acid, optionally after one or more workups, being separated by crystallization of acetic acid, the resultant mother liquor being separated from the crystallized acetic acid to obtain the solid crystallized acetic acid, which is preferably to be recycled into the process, and a liquid stream comprising acrylic acid and acetic acid, and this liquid stream being separated into at least an acrylic acid-depleted stream and an acrylic acid-enriched stream.

The present invention therefore relates to a process for obtaining acrylic acid, comprising
(a) providing a liquid stream S7 comprising acetic acid and acrylic acid, where the molar ratio of acetic acid to acrylic acid in stream S7 is greater than 1:1,
(b-1) crystallizing a portion of the acetic acid present in stream S7 to obtain solid crystallized acetic acid in its mother liquor,
(b-2) separating the mother liquor from the acetic acid crystallized in (b-1) to obtain the solid crystallized acetic acid and a liquid stream S8 comprising acrylic acid and acetic acid,
(c) separating stream S8 into at least one stream S10 depleted of acrylic acid compared to S8 and a stream S11 enriched in acrylic acid compared to S8.

This process of the invention, comprising the crystallization of the acetic acid and the subsequent separation, enables use of an excess of acetic acid to formaldehyde in the process for obtaining acrylic acid, in order to achieve the above-described increase in yield and simultaneously to make the process economically viable, especially by virtue of the unconverted acetic acid being recyclable into the process and hence reusable in an efficient manner.

Providing the Liquid Stream S7 in (a)

In step (a), a liquid stream S7 comprising acetic acid and acrylic acid is provided, where the molar ratio of acetic acid to acrylic acid in stream S7 is greater than 1:1. Preferably, the molar ratio of acetic acid to acrylic acid in stream S7 is in the range from 1.1:1 to 20:1, further preferably in the range from 1.5:1 to 17.5:1, further preferably in the range from 2:1 to 15:1, further preferably in the range from 2.5:1 to 12.5:1, further preferably in the range from 3:1 to 10:1.

Stream S7 may in principle assume any desired content of acetic acid and acrylic acid which allows crystallizing in (b-1), provided that the molar ratio of acetic acid to acrylic acid in stream S7 is greater than 1:1. Preferably, stream S7 consists of acetic acid and acrylic acid to an extent of 45% to 100% by weight, further preferably to an extent of 65% to 99.9% by weight, further preferably to an extent of 85% to 99.8% by weight, further preferably to an extent of 98% to 99.7% by weight.

In principle, it is possible that stream S7 comprises at least one further component in addition to acetic acid and acrylic acid. Thus, stream S7, in addition to acetic acid and acrylic acid, may comprise at least one component selected from the group consisting of formaldehyde, water, methanol, formic acid, propionic acid, acetone, acrolein, methyl acetate, methyl acrylate, methacrolein, and mixtures thereof. Preferably, stream S7, in addition to acetic acid and acrylic acid, comprises formaldehyde and water, with or without formic acid. Further preferably, stream S7 consists of acetic acid, acrylic acid, water, formaldehyde and any formic acid to an extent of 45% to 100% by weight, preferably to an extent of 65% to 99.9% by weight, further preferably to an extent of 85% to 99.8% by weight, further preferably to an extent of 98% to 99.7% by weight, based in each case on the total weight of stream S7.

The liquid stream S7 may in principle be provided at any temperature suitable for the process of the invention. Preferably, stream S7 is at a temperature in the range from 20 to 80° C., further preferably from 25 to 60° C., further preferably from 30 to 50° C., further preferably from 35 to 45° C. Further preferably, stream S7 is at a temperature in the range from 38 to 42° C. In principle, the liquid stream S7 can be provided at any pressure suitable for the present process.

Preferably, stream S7 is provided at a pressure in the range from 0.1 to 6 bar, preferably from 0.9 to 1.5 bar. Further preferably, stream S7 is therefore provided at a temperature of the stream in the range from 20 to 80° C. and a pressure in the range from 0.1 to 6 bar, further preferably at a temperature in the range from 35 to 45° C. and a pressure in the range from 0.9 to 1.5 bar.

All pressure figures in the context of the present invention relate to absolute pressures.

The liquid stream S7 can in principle be provided in any suitable manner. Useful sources for the acetic acid in principle include any suitable source comprising at least a proportion of acetic acid. This may be acetic acid supplied fresh to the process and/or acetic acid recycled from the process or a mixture thereof. Useful sources for the acrylic acid in principle include any suitable source comprising at least a proportion of acrylic acid. Thus, it is possible that the acrylic acid is at least partly formed in a chemical reaction during the present process. Preferably, the providing of stream S7 comprises the preparation of at least a portion of the acrylic acid present in stream S7. The acrylic acid can be prepared in any suitable chemical reaction, preference being given to obtaining the acrylic acid present in stream S7 by an aldol condensation of acetic acid and formaldehyde. In addition, the source of the acrylic acid may at least partly be acrylic acid recycled from the process.

Preferably, the liquid stream S7 is a stream which results directly from a preparation of acrylic acid by means of acetic acid, preferably by means of acetic acid and formaldehyde in an aldol condensation. The liquid stream S7 may likewise be a stream which results from one or more workup steps in which a stream that results directly from the preparation of acrylic acid by means of acetic acid, preferably acetic acid and formaldehyde in an aldol condensation, is worked up. For example, these workup steps may comprise one or more distillations and/or single or multiple cooling operations and/or single or multiple compression operations. For example, the liquid stream S7 can be obtained by cooling or compressing or cooling and compressing a gaseous stream or a plurality of gaseous streams, in which case the cooling or compressing or cooling and compressing can be conducted more than once. It is also possible for the liquid stream S7 to be obtained by separating a stream obtained by cooling or compressing or cooling and compressing a gaseous stream, for example by separation by rectification, for example distillation. Equally, the liquid stream S7 can be obtained by separating, for example by separating by rectification, for example distillation, from a stream obtained by cooling or compressing or cooling and compressing a gaseous stream.

Crystallizing in (b-1)

In step (b-1) of the process of the invention, a portion of the acetic acid present in stream S7 is crystallized to obtain solid crystallized acetic acid in its mother liquor. The crystallizing in (b-1) can be effected in continuous or batchwise mode. In addition, it is possible in principle to use any method for crystallization which is known to the person skilled in the art and is suitable in the present context, for instance cooling crystallization, evaporation crystallization and vacuum crystallization. Preferably, in the context of the present process, the crystallization is effected by cooling crystallization, i.e. by lowering the temperature of stream S7, i.e. of at least a portion of stream S7 in a continuous mode of crystallization, or of a suitably separated portion of stream S7 in a batchwise mode of crystallization. Preferably, the crystallizing in (b-1) is configured as a layer crystallization or suspension crystallization.

Layer Crystallization

Layer crystallization involves contacting the solution or the melt with cooled surfaces of a heat exchanger of a crystallizer. The heat exchanger surfaces of the crystallizer are typically cooled to temperatures of up to 40° C. below the melting temperature of acetic acid. On attainment of the desired amount of solids formed by cooling, the cooling operation is ended and the remaining liquid (mother liquor) is separated in (b-2), for example by pumping it off or allowing it to flow away. The purity of the crystals of acetic acid which remain on the heat exchanger surfaces of the crystallizer can be increased as described by washing, preferably with acetic acid, or sweating, or washing, preferably with acetic acid, and sweating.

The crystallized acetic acid is isolated by melting in (b-3) of the solid crystallized acetic acid removed to obtain stream S9, for example by heating the heat exchanger surfaces or by feeding in a melt of purified acetic acid or by heating the heat exchanger surfaces and feeding in a melt of purified acetic acid.

In the context of the present process, it is preferable that the crystallizing in (b-1) is effected by means of layer crystallization of at least one heat exchanger surface. The temperature required for layer crystallization depends on the degree of contamination. The upper limit is the equilibrium temperature at which the already crystallized acetic acid is at equilibrium with the acetic acid present in the mother liquor. According to the composition, the equilibrium temperature is in the range from 0.1 to 40 K below the melting temperature of pure acetic acid. In the context of the present process, it is therefore preferable that the at least one heat exchanger surface is at a temperature in the range from −35 to +16.5° C., preferably in the range from −30 to +10° C., further preferably in the range from −25 to +5° C.

The crystallization on cooling surfaces can be conducted as a dynamic or static process. In the case of the dynamic crystallization processes, the melt to be crystallized is kept in a flowing motion. This can be accomplished by forced flow in fully flooded heat exchangers or by means of a trickle film on a cooled wall. In the case of static crystallization, mass transfer takes place in the liquid phase only through free convection (melt at rest).

Static layer crystallization can be initiated by a seeding operation. For example, the liquid remaining as a residual film on the cooling surfaces after the melting may be partly or completely frozen on the cooling surface as seed crystals, and then another crystallization is conducted. Seed crystals can also be frozen by applying seed crystals to the cooling surface prior to the crystallization by contacting the cooling surface with a pure melt of acetic acid in a separate step and then forming corresponding seed crystals by cooling. Here too, the residual film remaining on the cooling surfaces is partly or completely frozen by lowering the temperature at the surfaces. It is also possible to produce a layer of seed crystals by contacting the cooling surface with a suspension of acetic acid containing crystals, in order to obtain a layer of seed crystals thereon by cooling the cooling surface after the majority of the suspension has been removed. It is likewise possible to achieve seeding by addition of crystals in solid form or in suspension form to the melt of acetic acid, in which case the melt is at a temperature close to or below the dissolution temperature. Seeding can also be achieved by producing or maintaining or producing and maintaining a crystal layer on a localized, separately cooled cooling surface (cold spot).

In order to enable a continuous process comprising (b-1) crystallizing a portion of the acetic acid present in stream S7 to obtain solid crystallized acetic acid in its mother liquor, preference is given to operating a plurality of crystallizers, for example two, three, four, five or more crystallizers, in parallel mode.

Suspension Crystallization

Equally preferably, the crystallizing in (b-1) is effected by means of suspension crystallization to obtain a suspension comprising solid crystallized acetic acid.

Suspension crystallization involves producing a crystal suspension in a solution or melt enriched in impurities by cooling the solution or melt. The crystals are dispersed in the liquid phase (mother liquor) and may grow directly in the suspension (melt) or be deposited as a layer on a cooled wall. On attainment of a desired crystal content, the crystals are subsequently scraped off this wall and suspended in the suspension (residual melt). The crystal suspension is preferably kept in motion during the process by pumped circulation or stirring, especially because of the high densities of solids in the suspension crystallization and the high temperature gradients which can lead to incrustation of the heat transfer surfaces.

As well as the simple stirred tanks or forced circulation crystallizers which are frequently used in solution crystallization, it is also possible to use other apparatuses, for example scraped coolers. In a scraped cooler, the layer of crystals which forms is produced in a jacketed tube through which the solution or melt flows on the inside and which is cooled on the outside, is removed by slow-rotating scraper elements, and is conveyed into the melt or solution. The crystals may subsequently pass through a growth zone in which they can grow further in the case of oversaturation. It is likewise possible to use cooling disk crystallizers. In this case, the crystals form on cooled disks which are immersed into the melt or solution and are continuously wiped off with the aid of scrapers.

As well as the suspension crystallization processes with indirect cooling by means of heat exchanger elements, the cooling of the suspension can also be implemented directly via the introduction of a coolant (for example of cold gases or liquids or evaporating liquids).

Suspension crystallization can be initiated by a seeding operation. Seeding can be achieved by addition of crystals in solid form or in suspension form to the melt of acetic acid, in which case the melt at the time of the addition is at a temperature close to or below the dissolution temperature of acetic acid. Seeding can also be achieved by producing and/or maintaining a crystal layer on a localized, separately cooled cooling surface (cold spot). Seed crystals can also be removed from such a separately cooled surface (for example mechanically, by means of flow forces or by ultrasound) and introduced into the melt of acetic acid.

Seed crystals can also be produced by first significantly cooling the liquid melt until crystal formation sets in spontaneously or with use of an above-described seeding operation, then the temperature of the suspension is raised again in order to melt a large portion of the crystals thus formed, and then cooling is effected in a slower and more controlled manner in the presence of the remaining residual crystals (seed crystals) in order to produce the desired suspension.

The suspension crystallization can be conducted batchwise or continuously.

In the case of a batchwise suspension crystallization, the crystallizing in (b-1) is effected on a volume taken from stream S7. In this case, the temperature of this volume taken is understood to mean the temperature to which the portion of stream S7 taken is cooled in (b-1). In the case of a continuous suspension crystallization, in the context of the present process, this temperature is understood such that at least a portion of stream S7, for example a stream S7 passed through a scraped cooler, is at this temperature.

Preferably, in the context of the present process, the crystallizing in (b-1) is conducted continuously as a suspension crystallization. In this context, preferably at least one scraped cooler is used. For example, it is possible to operate two, three, four or more scraped coolers in parallel mode or in NB mode.

Preferably, the crystallizing in (b-1) is effected by means of suspension crystallization to obtain a suspension comprising solid crystallized acetic acid, with cooling of at least a portion of stream S7 to a particular temperature, the end temperature. The end temperature is chosen such that solid crystallized acetic acid in its mother liquor is obtained in the desired amount. It is preferable that the crystallizing in (b-1) is effected by means of suspension crystallization to obtain a suspension comprising solid crystallized acetic acid, with cooling of at least a portion of stream S7 to an end temperature in the range from −35 to +17° C., preferably from −25 to +12° C., further preferably from −20 to +10° C.

The cooling can in principle be effected at any desired cooling rate and should be chosen such that solid crystallized acetic acid in the desired purity is obtained in its mother liquor. Preferably, the cooling rate of the at least one portion of stream S7 is in the range from 0.1 to 5 K/h, preferably from 0.5 to 2.5 K/h, further preferably from 0.7 to 1.3 K/h.

In principle, the solids content of the suspension comprising solid crystallized acetic acid in its mother liquor which is obtained by the crystallizing in (b-1) at the end temperature is not subject to any restrictions. Preferably, the solids content of the suspension obtained at the end temperature is in the range from 10% to 50% by weight, preferably from 20% to 40% by weight, further preferably from 25% to 35% by weight, based in each case on the at least one portion of stream S7.

Separating in (b-2)

In step (b-2), the mother liquor from the acetic acid crystallized in (b-1) is separated off to obtain the solid crystallized acetic acid and a liquid stream S8 comprising acrylic acid and acetic acid.

The separating in (b-2) can be effected by any method which is known to the person skilled in the art and is suitable in the present context for solid-liquid separation. Preferably, the separating in (b-2) is effected by means of centrifuging, filtering, decanting, spray-drying, pumping off, or a combination of two or more thereof, further preferably by means of centrifuging, filtering or a combination thereof.

Useful apparatuses for the separating in (b-2) include all apparatuses which are known to the person skilled in the art and are suitable in the present context for solid-liquid separation, for example suction filters, belt filters and centrifuges, such as drum centrifuges.

The mixture of mother liquor and solid crystallized acetic acid present therein which has been obtained in (b-1) can be subjected directly to the separating in (b-2). It is equally possible to thicken the mixture of mother liquor and solid crystallized acetic acid present therein which has been obtained in (b-1) prior to the separation in (b-2) by removing the liquid constituents and thus simplifying the separation in (b-2). Such a thickening operation can be effected with all apparatuses known to those skilled in the art, for example by means of a hydrocyclone.

In the process of the invention, (b-2) may comprise further steps as well as the separation and optional thickening, such as the washing of the solid crystallized acetic acid with one or more washing compositions. Useful washing compositions include all washing compositions suitable for the present process, and in the case of a plurality of washing compositions it is possible to use them as a mixture, successively or alternately. Preferably, the washing is effected with at least one washing composition comprising acetic acid. Further preferably, at least one washing composition has an acetic acid content of at least 90% by weight, further preferably at least 95% by weight, further preferably at least 98% by weight. Further preferably, the solid crystallized acetic acid is washed with at least one washing composition consisting of acetic acid, meaning that the washing composition comprises compounds other than acetic acid only in amounts resulting from impurities. Preferably, the separating in (b-2) consequently comprises the washing of the solid crystallized acetic acid with one or more washing compositions, further preferably comprising acetic acid, further preferably with acetic acid. Preferably, the separating in (b-2) consequently comprises the washing of the solid crystallized acetic acid with a washing composition consisting of acetic acid.

Equally, in the present process, (b-2) may comprise, as well as the separating and optional thickening and optional washing, the drying of the solid crystallized acetic acid. The drying of the solid crystallized acetic acid can be effected, for example, after the separating or between the separating and the washing or between the washing with a first washing composition and the washing with a second washing composition or between the separating and the washing with a first washing composition and between the washing with a first washing composition and the washing with a second washing composition, where the first and second washing compositions may be the same or different. The drying can be effected, for example, by a reduction in the pressure or by the treatment of the solid crystallized acetic acid with a gas stream, with the possibility of drying in a different way each time in the case of a plurality of drying steps. The gas stream for drying may comprise nitrogen, oxygen, carbon dioxide or a mixture of two or more thereof. The gas stream used for drying is preferably ambient air or synthetic air.

In the context of the present invention, it is possible that the sequence comprising (b-1) and (b-2) is conducted twice or more in succession. Preferably, the sequence of (b-1) and (b-2) is conducted at least once, preferably once.

The liquid stream S8 which comprises acrylic acid and acetic acid and is obtained in (b-2) is depleted in terms of its acetic acid content compared to stream S7 and therefore has a lower content of acetic acid. Preferably, the acetic acid content of stream S8 is in the range from 1% to 95% by weight, further preferably from 10% to 94% by weight, further preferably from 25% to 93% by weight, further preferably from 50% to 90% by weight, further preferably from 60% to 85% by weight.

The term "depleted" as used in the present context means that, through at least one workup step for a stream x, the stream y depleted in terms of a component i that results from the at least one workup step has a lower proportion by weight of component i than stream x. The term "enriched" as used in the context of the present invention means that, through at least one workup step for a stream x, the stream y enriched in terms of a component i that results from the at least one workup step has a higher proportion by weight of component i than stream x.

In principle, it is possible that stream S8 comprises at least one further component as well as acrylic acid and acetic acid. Preferably, stream S8, in addition to acrylic acid and acetic acid, comprises at least one compound selected from the group consisting of formaldehyde, water, methanol, formic acid, propionic acid, acetone, acrolein, methyl acetate, methyl acrylate and methacrolein, preferably formaldehyde, water and formic acid.

Melting in (b-3)

In principle, the solid crystallized acetic acid crystallized in (b-1) and separated in (b-2) can be sent to the further use thereof in the solid or liquid state, optionally after one or more workup steps which follow on from (b-2).

Preferably, the solid crystallized acetic acid crystallized in (b-1) and separated in (b-2) is sent to further use thereof in the liquid state. It is preferable here that the solid crystallized acetic acid separated in (b-2), optionally after one or more workup steps which follow on from (b-2), is melted by heating to obtain a stream S9.

The temperature to which the solid crystallized acetic acid separated in (b-2) is heated for melting may in principle assume any value which is above the melting point of acetic acid but at which no breakdown of the acetic acid takes place. If the acetic acid comprises impurities, which may lead to the formation of a eutectic mixture, it is equally possible in the context of the present process that a temperature below the melting point of pure acetic acid will be sufficient to melt the solid crystallized acetic acid separated in (b-2) and hence to convert it to the liquid state. Preferably, the solid crystallized acetic acid separated in (b-2), for melting, is heated to a temperature in the range from 10 to 30° C., preferably from 15 to 20° C., to obtain a stream S9.

Preferably, the process of the invention therefore additionally comprises (b-3) optionally after one or more workup steps which follow on from (b-2), melting the solid crystallized acetic acid separated in (b-2), preferably by heating to a temperature in the range from 10 to 30° C., preferably from 15 to 20° C., to obtain a stream S9.

Accordingly, the present invention also relates to a process for obtaining acrylic acid, comprising (a) providing a liquid stream S7 comprising acetic acid and acrylic acid, where the molar ratio of acetic acid to acrylic acid in stream S7 is greater than 1:1, (b-1) crystallizing a portion of the acetic acid present in stream S7 to obtain solid crystallized acetic acid in its mother liquor, (b-2) separating the mother liquor from the acetic acid crystallized in (b-1) to obtain the solid crystallized acetic acid and a liquid stream S8 comprising acrylic acid and acetic acid, (b-3) optionally after one or more workup steps which follow on from (b-2), melting the solid crystallized acetic acid separated in (b-2), preferably by heating to a temperature in the range from 10 to 30° C., preferably from 15 to 20° C., to obtain a stream S9, (c) separating stream S8 into at least one stream S10 depleted of acrylic acid compared to S8 and a stream S11 enriched in acrylic acid compared to S8.

In order to increase the acetic acid content of stream S9, the melting in (b-3) is preferably conducted in such a way that the solid crystallized acetic acid separated in (b-2) is partly melted and this molten acetic acid is separated from the non-molten acetic acid, before the remaining non-molten acetic acid is melted to obtain stream S9. Preferably, the melting in (b-3) therefore comprises (b-3.1) melting a portion, preferably from 0.1% to 5% by weight, further preferably from 0.5% to 3% by weight, of the solid crystallized acetic acid separated in (b-2), (b-3.2) separating the acetic acid melted in (b-3.1) from the non-molten acetic acid, (b-3.3) melting the non-molten acetic acid obtained in (b-3.2), preferably by heating to a temperature in the range from 10 to 30° C., preferably from 15 to 20° C., to obtain stream S9.

Accordingly, the present invention also relates to a process for obtaining acrylic acid, comprising
(a) providing a liquid stream S7 comprising acetic acid and acrylic acid, where the molar ratio of acetic acid to acrylic acid in stream S7 is greater than 1:1,
(b-1) crystallizing a portion of the acetic acid present in stream S7 to obtain solid crystallized acetic acid in its mother liquor,
(b-2) separating the mother liquor from the acetic acid crystallized in (b-1) to obtain the solid crystallized acetic acid and a liquid stream S8 comprising acrylic acid and acetic acid,
(b-3) optionally after one or more workup steps which follow on from (b-2), melting the solid crystallized acetic acid separated in (b-2), preferably by heating to a temperature in the range from 10 to 30° C., preferably from 15 to 20° C., to obtain a stream S9,
(c) separating stream S8 into at least one stream S10 depleted of acrylic acid compared to S8 and a stream S11 enriched in acrylic acid compared to S8,
where the melting in (b-3) comprises:
(b-3.1) melting a portion, preferably from 0.1% to 5% by weight, further preferably from 0.5% to 3% by weight, of the solid crystallized acetic acid separated in (b-2),
(b-3.2) separating the acetic acid melted in (b-3.1) from the non-molten acetic acid,
(b-3.3) melting the non-molten acetic acid obtained in (b-3.2), preferably by heating to a temperature in the range from 10 to 30° C., preferably from 15 to 20° C., to obtain stream S9.

Preferably, the acetic acid content of the stream S9 obtained in (b-3) is from 80% to 99.999% by weight, preferably from 85% to 99% by weight, further preferably from 90% to 98.5% by weight.

Stream S9 is not restricted in principle in terms of the further use thereof. For example, it is possible that stream S9 is at least partly fed to a process other than the present process or is at least partly recycled into the present process. Preferably, stream S9, optionally after one or more workups, is at least partly recycled into the process of the invention, preferably to an extent of 50% to 100% by weight, further preferably to an extent of 75% to 100% by weight, further preferably to an extent of 95% to 100% by weight. More preferably, stream S9, optionally after one or more workups, is recycled completely into the process of the invention.

Accordingly, the present invention also relates to a process for obtaining acrylic acid, comprising
(a) providing a liquid stream S7 comprising acetic acid and acrylic acid, where the molar ratio of acetic acid to acrylic acid in stream S7 is greater than 1:1,
(b-1) crystallizing a portion of the acetic acid present in stream S7 to obtain solid crystallized acetic acid in its mother liquor,
(b-2) separating the mother liquor from the acetic acid crystallized in (b-1) to obtain the solid crystallized acetic acid and a liquid stream S8 comprising acrylic acid and acetic acid,
(b-3) optionally after one or more workup steps which follow on from (b-2), melting the solid crystallized acetic acid separated in (b-2), preferably by heating to a temperature in the range from 10 to 30° C., preferably from 15 to 20° C., to obtain a stream S9,
(c) separating stream S8 into at least one stream S10 depleted of acrylic acid compared to S8 and a stream S11 enriched in acrylic acid compared to S8,
with recycling of stream S9, optionally after one or more workups, into the process for obtaining acrylic acid to an extent of 95% to 100% by weight.

In the context of the present process, it is possible that the sequence comprising (b-1) (b-2) (b-3) is conducted twice or more in succession. Preferably, the sequence of (b-1) (b-2) (b-3) is conducted at least once, preferably once.

If the sequence comprising (b-1) and (b-2) or the sequence comprising (b-1), (b-2) and (b-3) is conducted more than once, the respective crystallizing in a given sequence can be conducted independently of the crystallizing in another sequence as a layer crystallization or suspension crystallization.

Separating in (c)

The stream S8 obtained in (b-2) is subjected to at least one workup in which stream S8 is separated into at least two, preferably two or three, streams. The process of the invention therefore additionally comprises
(c) separating stream S8 into at least one stream S10 depleted of acrylic acid compared to S8 and a stream S11 enriched in acrylic acid compared to S8.

With regard to the separating in (c), this can be effected by any method or combination of methods which is known to the person skilled in the art and is suitable in the present context. Preferably, the separating in (c) is effected by distillation, further preferably by rectification. For rectificative separation, it is possible in principle to use any suitable apparatus or any suitable combination of apparatuses. Preference is given here to using at least one column, further preferably one or two columns, further preferably one column, having separating internals in accordance with the invention.

The term "separating internals" as used in the context of the present invention is understood to mean crossflow or mass transfer trays, for example bubble-cap trays, valve trays, sieve trays, grid trays, dual flow trays, Thormann trays, tunnel-cap trays, and also structured packings and unstructured random packings. Equally conceivable are combinations of at least one tray type and structured packings or random packings or combinations of at least one tray type and structured packings and random packings, in which case the separating internals or combinations of two or more thereof may vary along the longitudinal axis or along the cross section of the column or along the longitudinal axis and along the cross section of the column.

Preferably, the separating in (c) is effected by rectificative means, preferably using at least one column, further preferably one or two columns, further preferably one column, preferably a tray column, equipped with separating internals, preferably dual-flow trays.

In principle, the at least one column for the separating in (c) is not restricted in terms of theoretical plates, provided that the described separating in (c) is achieved. Preferably, the at least one column operated by rectificative means has 5 to 40, further preferably 10 to 20, further preferably 11 to 15, theoretical plates.

In principle, stream S8 can be fed in in the stripping section of the column or in the rectifying section of the column. Preferably, stream S8 is fed to the column in (c) in the region between the 5th and 15th theoretical plates, preferably at the 12th theoretical plate.

In principle, the separating in (c) can be effected at any suitable pressure. Preferably, the separating in (c) is effected at a pressure at the top of the column in the range from 0.01 to 0.5 bar, preferably in the range from 0.02 to 0.08 bar, further preferably in the range from 0.04 to 0.06 bar.

Equally, the separating in (c) can in principle be effected at any suitable temperature. Preferably, the separating in (c) is effected at a temperature in the bottom of the column in the range from 60 to 105° C., preferably in the range from 70 to 95° C., further preferably in the range from 80 to 85° C.

Preferably, the separating in (c) is conducted at a pressure at the top of the column in the range from 0.01 to 0.5 bar and at a temperature in the bottom of the column in the range from 60 to 105° C., further preferably from 0.02 to 0.08 bar and from 70 to 95° C., further preferably from 0.04 to 0.06 bar and 80 to 85° C.

In principle, stream S10 can be withdrawn in the stripping section of the column, in the rectifying section of the column or from the top of the column. Preferably, stream S10 is withdrawn from the top of the column in (c).

In principle, stream S11 can be withdrawn in the rectifying section of the column or in the bottom of the column. Preferably, stream S11 is drawn off in gaseous form above the bottom and then condensed.

The stream S11 which has been enriched in acrylic acid compared to S8 is not restricted in principle with regard to further components present and may, as well as acrylic acid, comprise at least one further component selected from the group consisting of acetic acid, water, formic acid and propionic acid and a mixture of at least two thereof. Preferably, stream S11 comprises at least 90% by weight of acrylic acid, further preferably at least 95% by weight, further preferably at least 98% by weight, further preferably at least 98.5% by weight.

Stream S11 is not restricted in principle in terms of the further use thereof. Thus, this stream S11 enriched in acrylic acid compared to S8, optionally after one or more workups, can be withdrawn as a product stream from the present process for obtaining acrylic acid. Stream S11 can likewise be sent to a further distillative separation or to a crystallization or to a further distillative workup and a crystallization, in order to increase the purity of the acrylic acid.

Preferably, as well as streams S10 and S11, at least one further stream, preferably one further stream, is withdrawn from the column in (c). Thus, it is preferable in the context of the present process that, in the bottom of the column in (c), high-boiling components such as acrylic acid dimer or acrylic acid oligomers are drawn off in liquid form as stream S12 and optionally fed to an oligomer splitting operation. Stream S12 preferably comprises at least 95% by weight of acrylic acid, acrylic acid dimer and acrylic acid oligomers, further preferably at least 98% by weight, further preferably at least 99% by weight.

Aldol Condensation

As described above, the acrylic acid present in stream S7 or at least a portion thereof is preferably obtained by an aldol condensation of acetic acid and formaldehyde. Preferably, stream S7 comes from an aldol condensation, further preferably from an aldol condensation and one or more subsequent workups, further preferably from an aldol condensation of acetic acid and formaldehyde and one or more subsequent workups.

Further preferably, the providing of the liquid stream S7 in (a) comprises (a-1) providing a gaseous stream S3 comprising acetic acid, formaldehyde and optionally inert gas, (a-2) contacting stream S3 with an aldol condensation catalyst to obtain a stream S4 comprising acetic acid and acrylic acid, preferably acetic acid, acrylic acid, water and formaldehyde, (a-3) optionally separating stream S4 to obtain a stream S5 comprising inert gas and a stream S6 comprising acetic acid and acrylic acid, or comprising acetic acid, acrylic acid, water, formaldehyde and any formic acid, (a-4) optionally separating stream S6 to obtain a stream S15 enriched in formaldehyde compared to S6 and a stream S7 depleted of formaldehyde compared to S6, where, if (a-3) is not conducted and (a-4) is conducted, S4 is the same as S6;

where, if (a-4) is not conducted and (a-3) is conducted, S6 is the same as S7;

where, if neither (a-3) nor (a-4) is conducted, S4 is the same as S7.

Providing in (a-1)

The gaseous stream S3 provided with preference in (a-1) comprises acetic acid, formaldehyde and optionally inert gas, and preferably has a molar ratio of acetic acid to formaldehyde of greater than 1:1. Further preferably, the molar ratio of acetic acid to formaldehyde in stream S3 is in the range from 1.1:1 to 10:1, further preferably from 1.5:1 to 8:1, further preferably from 1.9:1 to 4.1:1 or from 1.8:1 to 2.2:1 or from 3.8:1 to 4.2:1.

It is possible in principle that stream S3 consists of acetic acid and formaldehyde. Preferably, stream S3, as well as acetic acid and formaldehyde, comprises at least one further compound, further preferably water or inert gas or water and inert gas. In this context, the term "inert gas" is understood to mean all the materials that are gaseous under the process conditions chosen in each case and are inert in both stages (a-1) and (a-2). The term "inert" in this context means that the gaseous material in a single pass through the particular reaction stage is converted to an extent of less than 5 mol %, preferably to an extent of less than 2 mol %, more preferably to an extent of less than 1 mol %. The term "inert gas" as used in the present context refers either to a single gas or to a mixture of two or more gases. For example, useful inert gases include helium, neon, argon, krypton, xenon, nitrogen, sulfur hexafluoride and mixtures of two or more thereof. Preferably, the inert gas comprises nitrogen, there being no restrictions in principle with regard to the proportion of nitrogen. If the inert gas comprises nitrogen, preferably at least 95% by weight, further preferably at least 98% by weight, further preferably at least 99% by weight, of the inert gas consists of nitrogen. More preferably, the inert gas consists of nitrogen. In this context of the present invention, water, carbon monoxide, carbon dioxide, hydrogen, methylene glycol, hemiformal, acetaldehyde, methyl acrylate, methyl acetate, ethene, acetone and methyl formate are not covered by the term "inert gas".

In principle, stream S3, as well as acetic acid, formaldehyde, water or inert gas or water and inert gas, may comprise further components. Stream S3 may thus comprise at least one further component selected from the group consisting of acrylic acid, methanol, formic acid, propionic acid, acetone, acetaldehyde, acrolein, methyl acetate, methyl acrylate, methacrolein, ethylene, carbon dioxide, oxygen and carbon monoxide.

Preferably, stream S3 consists of acetic acid, formaldehyde, water and inert gas to an extent of 50% to 99% by weight, preferably to an extent of 70% to 99.5% by weight, further preferably to an extent of 85% to 99% by weight.

As described, stream S9 is not restricted in principle in terms of the further use thereof. For example, it is possible that stream S9 is at least partly fed to a process other than the process of the invention or is at least partly recycled into the process of the invention. Preferably, stream S9, optionally after one or more workups, is at least partly recycled into the process of the invention, preferably to an extent of 50% to 100% by weight, further preferably to an extent of 75% to 100% by weight, further preferably to an extent of 95% to 100% by weight. Preferably, stream S9 is at least partly recycled into (a-1), preferably to an extent of 50% to 100% by weight, further preferably to an extent of 75% to 100% by weight, further preferably to an extent of 95% to 100% by weight. More preferably, stream S9 is recycled completely into (a-1).

Contacting in (a-2)

In (a-2), the gaseous stream S3 is contacted with an aldol condensation catalyst to obtain a stream S4 which is preferably obtained in gaseous form, comprising acetic acid and acrylic acid, preferably acetic acid, acrylic acid, water and formaldehyde, with or without formic acid.

The term "aldol condensation catalyst" as used in this context of the present process is understood to mean any catalyst capable of catalyzing an aldol condensation of the two compounds formaldehyde and acetic acid to give acrylic acid.

In principle, all suitable aldol condensation catalysts are useful in accordance with the invention. Examples, used as unsupported catalysts or in supported form, are alkali metal or alkaline earth metal oxides, mixed oxides comprising vanadium oxide, aluminosilicates or zeolites. Preferably, the aldol condensation catalyst in (a-2) comprises vanadium and optionally phosphorus, further preferably vanadium and phosphorus, further preferably a vanadium-phosphorus oxide. Further preferably, the aldol condensation catalyst in (a-2) comprises a vanadium-phosphorus oxide having the general empirical formula $V_2O_x(PO_4)_y$ where x is preferably in the range from 1.0 to 2.75, further preferably from 1.5 to 2.25, and y is preferably in the range from 1.5 to 2.5, further preferably from 1.8 to 2.3.

Preferably, the aldol condensation catalyst in (a-2) is in the form of an unsupported catalyst or in supported form on at least one support material. If the aldol condensation catalyst in (a-2) is present in supported form on at least one support material, the at least one support material is preferably selected from the group consisting of $SiO_2$, $TiO_2$, $Al_2O_3$ and $ZrO_2$ and mixtures of two or more thereof.

The aldol condensation catalyst in (a-2) may be present, for example, as granules or extrudates in the form of cylinders, spheres, hollow cylinders, in star form, in tablet form or as a mixture thereof. Preferably, the aldol condensation catalyst in (a-2) is in the form of extrudates, the cross section of the extrudates having a rectangular, triangular, hexagonal, square, polygonal, oval or circular shape. Particular preference is given to using an aldol condensation catalyst in extrudates with a round cross section, the diameter of the round cross-sectional area being in the range from 0.1 to 100 mm, preferably in the range from 0.2 to 80 mm, further preferably in the range from 0.5 to 50 mm, further preferably in the range from 1 to 30 mm, and at the same time, for each of the aforementioned cases, the length of the extrudates being in the range from 0.1 to 100 mm, preferably in the range from 0.5 to 80 mm, further preferably in the range from 1 to 70 mm.

The contacting in (a-2) is preferably effected in at least one reactor, further preferably in at least two reactors, for example two, three, four or five reactors, where at least two reactors may be arranged in parallel or at least two reactors in series or at least two reactors in parallel and at least two reactors in series.

It is likewise possible that at least two, preferably two, three, four or five, further preferably two, three or four, further preferably two or three, further preferably two, reactors connected in parallel are used in alternation, with at least one reactor always in operation in this alternating mode of operation. Preferably, the contacting in (a-2) is effected in at least one reactor, preferably at least two reactors, further preferably in at least two reactors connected in parallel, which are further preferably operated in alternation. Preferably, these reactors are configured as fixed bed reactors, for example as shell and tube reactors or thermoplate reactors. In the case of a shell and tube reactor, the catalytically active fixed bed is advantageously within the catalyst tubes, with fluid heat carrier flowing around them.

The catalyst hourly space velocity with regard to the contacting in (a-2) in the reactor is preferably chosen such that a balanced ratio of the parameters of conversion, selectivity, yield, reactor geometry and reactor dimensions can be achieved, the catalyst hourly space velocity with regard to the contacting in (a-2) in the reactor being defined as mass of S3 in kg per hour and per unit mass of aldol condensation catalyst in kg. Preferably, the contacting in (a-2) in the fixed bed reactor is effected at a catalyst hourly space velocity in the range from 0.01 to 50 kg/(h*kg), further preferably in the range from 0.1 to 40 kg/(h*kg), further preferably in the range from 0.5 to 30 kg/(h*kg).

The contacting in (a-2) in the reactor is not subject to any particular restrictions with regard to the temperature of the catalyst bed, provided that the contacting of stream S3 with the aldol condensation catalyst in (a-2) gives a stream S4 comprising acetic acid and acrylic acid, preferably acetic acid, acrylic acid, water and formaldehyde. Preferably, the contacting in (a-2) in the reactor is effected at a temperature of the catalyst bed in the range from 200 to 450° C., further preferably in the range from 250 to 400° C., further preferably in the range from 290 to 380° C.

The contacting in (a-2) is not subject to any particular restrictions with regard to the pressure in the reactor, provided that the contacting of stream S3 with the aldol condensation catalyst in (a-2) gives a stream S4 comprising acetic acid and acrylic acid, preferably acetic acid, acrylic acid, water and formaldehyde. Preferably, the contacting in (a-2) in the reactor is effected at a pressure in the range from 0.5 to 5 bar, further preferably in the range from 0.8 to 3 bar, further preferably in the range from 1 to 1.8 bar.

Preferably, the contacting in (a-2) in the reactor is effected at a temperature of the catalyst bed in the range from 200 to 450° C. and a pressure of 0.5 to 5 bar, further preferably at a temperature of 290 to 380° C. and a pressure of 0.8 to 3 bar, further preferably at a temperature of 250 to 400° C. and a pressure of 1 to 1.8 bar.

In the context of the process of the invention, it is possible that the stream S4 obtained in (a-2), either without prior cooling or after prior cooling, is stored intermediately in one or more buffer vessels, preferably in one buffer vessel, before it is used further. One reason why intermediate storage is preferable is in order to balance out any possible slight variations in the composition of stream S4 which may occur in the course of operation of the overall process, which is preferably continuous in accordance with the invention, and thus to ensure that a downstream process stage is supplied continuously with a stream having a comparatively more constant composition over time. According to the design of the overall process, it is preferable, for example, to intermediately store an amount of stream S4 which occurs over a period in the range from 1 to 20 h, preferably from 5 to 15 h, further preferably from 8 to 12 h, in one or more than one buffer vessel. The one or more than one buffer vessel is generally kept at the feed temperature or a temperature below the feed temperature.

The stream S4 obtained in (a-2) may in principle be fed to step (b-1) as stream S7 directly, optionally after a dwell time in a buffer vessel, in which case the conversion of the stream S4 preferably obtained in gaseous form to the liquid state is required. For this purpose, all methods which are known to the person skilled in the art and are suitable in the present context are useful, such as cooling, compression and cooling, and compression, where cooling and compression may also be conducted more than once. In the case that neither (a-3) nor (a-4) is conducted, S4 is thus the same as S7 in terms of its physical composition.

Separating in (a-3)

Preferably, the stream S4 obtained in (a-2), optionally after the dwell time in a buffer vessel, is subjected to at least one workup before it is fed to step (b-1).

Thus, it is preferable in the context of the process of the invention that the stream S4 obtained in (a-2) is separated to obtain a stream S5 comprising inert gas and a stream S6 comprising acetic acid and acrylic acid, or comprising acetic acid, acrylic acid, water, formaldehyde and any formic acid. The stream S6 thus obtained can be fed to step (b-1) directly as stream S7 or be fed to at least one further workup and then fed at least partly to step (b-1) as stream S7.

Preferably, stream S4 is cooled by means of one or more heat exchanger(s) to a temperature in the range from −33 to 160° C., for which it is possible to use all suitable heat exchangers known to those skilled in the art, such as shell and tube heat transferers, plate heat transferers, pocket heat transferers and spiral heat transferers. It is preferable that stream S4 is cooled to a temperature at which it partly condenses and is thus separated into a gaseous stream S5 comprising inert gas and a liquid stream S6 comprising acetic acid and acrylic acid, or comprising acetic acid, acrylic acid, water, formaldehyde and any formic acid.

It is thus preferable in the context of the present process that the separating in (a-3) comprises the cooling of stream S4 to a temperature in the range from −33 to 160° C. and the condensing of at least a portion of stream S4 to obtain a gaseous stream S5 and a liquid stream S6.

The gaseous stream S5 is not restricted in terms of the further use thereof. In principle, it is possible that stream S5, optionally after one or more workups, is withdrawn from the process as offgas as stream S5a, fed to a process other than the present process or recycled as stream Opt2 in the present process. It is equally possible that stream S5, optionally after one or more workups, is partly withdrawn from the process as offgas as stream S5a and the remaining portion is recycled as stream Opt2 in the present process.

Preferably, the gaseous stream S5, optionally after one or more workups, is at least partly recycled as stream Opt2 in the present process. Further preferably, the gaseous stream S5, optionally after one or more workups, is recycled into the process as stream Opt2 to an extent of 10% to 100% by weight, further preferably to an extent of 20% to 70% by weight, further preferably to an extent of 25% to 45% by weight, while the remainder in each case is withdrawn from the process as offgas as stream S5a.

In principle, there is no restriction here as to the process stage into which the gaseous stream Opt2 is at least partly recycled, optionally after one or more workups. Preferably, stream Opt2 is at least partly recycled into (a-1), preferably to an extent of 50% to 100% by weight, further preferably to an extent of 75% to 99% by weight, further preferably to an extent of 80% to 98% by weight.

Separating in (a-4)

It is equally preferable in the context of the present process that the stream S4 obtained in (a-2) is separated as stream S6 to obtain a stream S15 enriched in formaldehyde compared to S6 and a stream S7 depleted of formaldehyde compared to S6.

With regard to the separating in (a-4), this can be effected by any suitable method or combination of methods known to the person skilled in the art. Preferably, the separating in (a-4) is effected by rectification. For rectificative separation, it is possible in principle to use any suitable apparatus or any suitable combination of apparatuses. Preference is given here to using at least one column, further preferably one or two columns, further preferably one column, having separating internals in accordance with the invention. Particular preference is given to using one column operated as a rectification column with separating internals; further preference is given to using a column operated as a rectification column and having mass transfer trays as separating internals.

Preferably, the separating in (a-4) is effected by rectificative means, preferably using at least one column, further preferably one or two columns, further preferably one column, preferably a tray column, preferably equipped with separating internals, preferably with crossflow trays.

In principle, the at least one column for the separating in (a-4) is not restricted in terms of theoretical plates, provided that the described separating in (a-4) is achieved. Preferably, the at least one column has 10 to 80, further preferably 25 to 60, further preferably 32 to 38, theoretical plates.

In principle, stream S6 can be fed in in the stripping section of the column or in the rectifying section of the column. Preferably, stream S6 is fed to the column in (a-4) in the region between the 10th and 20th theoretical plates, preferably at the 15th theoretical plate.

In principle, the separating in (a-4) can be effected at any suitable pressure. Preferably, the separating in (a-4) is effected at a pressure at the top of the column in the range from 0.1 to 2 bar, further preferably from 0.7 to 1.5 bar, further preferably from 0.9 to 1.3 bar.

Equally, the separating in (a-4) can in principle be effected at any suitable temperature. Preferably, the separating in (a-4) is effected at a temperature in the bottom of the column in the range from 100 to 200° C., further preferably in the range from 120 to 140° C.

Preferably, the separating in (a-4) is conducted at a pressure at the top of the column in the range from 0.1 to 2 bar and at a temperature in the bottom of the column in the range from 100 to 200° C., further preferably from 0.9 to 1.3 bar and 120 to 140° C.

In principle, stream S7 can be withdrawn in the stripping section of the column, in the rectifying section of the column or from the bottom of the column. Preferably, stream S7 is withdrawn from the bottom of the column.

In principle, stream S15 can be withdrawn in the stripping section of the column in (a-4), in the rectifying section of the column or from the top of the column. Preferably, stream S15 is withdrawn from the top of the column.

The stream S15 obtained from the column in (a-4) is not restricted in principle in terms of the further use thereof. For example, it is possible that stream S15 is at least partly sent to a process other than that according to the invention. In addition, it is possible that stream S15 is at least partly recycled into the present process, optionally after one or more workups.

Preferably, the stream S15 obtained in (a-4) is condensed virtually completely in a shell and tube apparatus, a portion of the condensate is recycled into the column in (a-4) to the uppermost tray as a liquid return stream S15b, the remaining portion of the condensate is conducted into the column in (e) as stream S15a, and the uncondensed portion is at least partly removed as offgas from the process as stream Opt3 and/or at least partly recycled into the present process, preferably into (a-1), as stream Opt4, optionally after one or more workups. Stream Opt4 advantageously serves here as recycled nitrogen and oxygen source. It is therefore preferable to cool the stream S15 withdrawn at the top of the column in (a-4) to a temperature in the range from −5 to 120° C., preferably 90 to 110° C., to recycle a portion of the condensate into the column in (a-4) to the uppermost tray as a liquid return stream S15b, and to conduct the other portion of the condensate into the column in (e) as stream S15a, while the uncondensed portion is at least partly removed as offgas from the process as stream Opt3 and/or at least partly recycled into the present process, preferably into (a-1), as stream Opt4, optionally after one or more workups.

Just like the direct feeding of stream S4 to the column in (a-4) as stream S6, it is preferable in the context of the present process that the stream S4 obtained in (a-2) is first separated in (a-3) to obtain a stream S5 comprising inert gas and a stream S6 comprising acetic acid and acrylic acid, or comprising acetic acid, acrylic acid, water, formaldehyde and any formic acid, and stream S6 is subsequently separated in (a-4) to obtain a stream S15 enriched in formaldehyde compared to S6 and a stream S7 depleted of formaldehyde compared to S6.

The present invention therefore also relates to a process for obtaining acrylic acid, comprising
(a) providing a liquid stream S7 comprising acetic acid and acrylic acid, where the molar ratio of acetic acid to acrylic acid in stream S7 is greater than 1:1,
(b-1) crystallizing a portion of the acetic acid present in stream S7 to obtain solid crystallized acetic acid in its mother liquor,
(b-2) separating the mother liquor from the acetic acid crystallized in (b-1) to obtain the solid crystallized acetic acid and a liquid stream S8 comprising acrylic acid and acetic acid,
(b-3) optionally after one or more workup steps which follow on from (b-2), melting the solid crystallized acetic acid separated in (b-2), preferably by heating to a temperature in the range from 10 to 30° C., preferably from 15 to 20° C., to obtain a stream S9,
(c) separating stream S8 into at least one stream S10 depleted of acrylic acid compared to S8 and a stream S11 enriched in acrylic acid compared to S8,
where the providing of the liquid stream S7 in (a) comprises:
(a-1) providing a gaseous stream S3 comprising acetic acid, formaldehyde and optionally inert gas,
(a-2) contacting stream S3 with an aldol condensation catalyst to obtain a stream S4 comprising acetic acid and acrylic acid, preferably acetic acid, acrylic acid, water and formaldehyde,
(a-3) separating stream S4 to obtain a stream S5 comprising inert gas and a stream S6 comprising acetic acid and acrylic acid, or comprising acetic acid, acrylic acid, water, formaldehyde and any formic acid,
(a-4) separating stream S6 to obtain a stream S15 enriched in formaldehyde compared to S6 and a stream S7 depleted of formaldehyde compared to S6.

The present invention therefore also relates to a process for obtaining acrylic acid, comprising
(a) providing a liquid stream S7 comprising acetic acid and acrylic acid, where the molar ratio of acetic acid to acrylic acid in stream S7 is greater than 1:1,
(b-1) crystallizing a portion of the acetic acid present in stream S7 to obtain solid crystallized acetic acid in its mother liquor,
(b-2) separating the mother liquor from the acetic acid crystallized in (b-1) to obtain the solid crystallized acetic acid and a liquid stream S8 comprising acrylic acid and acetic acid,
(b-3) optionally after one or more workup steps which follow on from (b-2), melting the solid crystallized acetic acid separated in (b-2), preferably by heating to a temperature in the range from 10 to 30° C., preferably from 15 to 20° C., to obtain a stream S9,
(c) separating stream S8 into at least one stream S10 depleted of acrylic acid compared to S8 and a stream S11 enriched in acrylic acid compared to S8,
where the providing of the liquid stream S7 in (a) comprises:
(a-1) providing a gaseous stream S3 comprising acetic acid, formaldehyde and optionally inert gas,
(a-2) contacting stream S3 with an aldol condensation catalyst to obtain a stream S4 comprising acetic acid and acrylic acid, preferably acetic acid, acrylic acid, water and formaldehyde,
(a-3) separating stream S4 to obtain a stream S5 comprising inert gas and a stream S6 comprising acetic acid and acrylic acid, or comprising acetic acid, acrylic acid, water, formaldehyde and any formic acid,
(a-4) separating stream S6 to obtain a stream S15 enriched in formaldehyde compared to S6 and a stream S7 depleted of formaldehyde compared to S6,
and where the melting in (b-3) comprises:
(b-3.1) melting a portion, preferably from 0.1% to 5% by weight, further preferably from 0.5% to 3% by weight, of the solid crystallized acetic acid separated in (b-2),
(b-3.2) separating the acetic acid melted in (b-3.1) from the non-molten acetic acid,
(b-3.3) melting the non-molten acetic acid obtained in (b-3.2), preferably by heating to a temperature in the range from 10 to 30° C., preferably from 15 to 20° C., to obtain stream S9.

Recycling from column in (c)

The stream S10 obtained from the column in (c) is not subject to any restriction in principle in terms of the further use thereof. Thus, stream S10 can be at least partly removed from the process and at least partly, optionally after one or more workups, recycled into the process of the invention. Preferably, stream S10 is at least partly recycled into the process of the invention, preferably into the column in (a-4).

Preferably, for this purpose, stream S10 is condensed virtually completely in a shell and tube apparatus, a portion of the condensate is recycled as liquid return stream S10b to the uppermost tray of the column in (c), the other portion of the condensate is recycled as stream S10a into the column in (a-4), and the uncondensed portion is discharged as offgas as stream S20. It is therefore preferable to cool the stream S10 withdrawn from the column in (c) at the top to a temperature in the range from 20 to 120° C., preferably 30 to 50° C., to recycle a portion of the condensate to the uppermost tray of the column in (c) as liquid return stream S10b, and to recycle the other portion of the condensate into the column in (a-4)

as stream S10a. Preferably, the weight ratio of stream S10b to stream S10a is from 0.1 to 3, further preferably from 0.3 to 1.5, further preferably from 0.5 to 0.7. In the context of the present invention, it is preferable that at least a portion, preferably 50% to 100% by weight, further preferably 75% to 99% by weight, further preferably 80% to 98% by weight, of stream S10a is recycled into the column in (a-4).

The present invention therefore also relates to a process for obtaining acrylic acid, comprising
(a) providing a liquid stream S7 comprising acetic acid and acrylic acid, where the molar ratio of acetic acid to acrylic acid in stream S7 is greater than 1:1,
(b-1) crystallizing a portion of the acetic acid present in stream S7 to obtain solid crystallized acetic acid in its mother liquor,
(b-2) separating the mother liquor from the acetic acid crystallized in (b-1) to obtain the solid crystallized acetic acid and a liquid stream S8 comprising acrylic acid and acetic acid,
(b-3) optionally after one or more workup steps which follow on from (b-2), melting the solid crystallized acetic acid separated in (b-2), preferably by heating to a temperature in the range from 10 to 30° C., preferably from 15 to 20° C., to obtain a stream S9,
(c) separating stream S8 into at least one stream S10 depleted of acrylic acid compared to S8 and a stream S11 enriched in acrylic acid compared to S8,
where the providing of the liquid stream S7 in (a) comprises:
(a-1) providing a gaseous stream S3 comprising acetic acid, formaldehyde and optionally inert gas,
(a-2) contacting stream S3 with an aldol condensation catalyst to obtain a stream S4 comprising acetic acid and acrylic acid, preferably acetic acid, acrylic acid, water and formaldehyde,
(a-3) separating stream S4 to obtain a stream S5 comprising inert gas and a stream S6 comprising acetic acid and acrylic acid, or comprising acetic acid, acrylic acid, water, formaldehyde and any formic acid,
(a-4) separating stream S6 to obtain a stream S15 enriched in formaldehyde compared to S6 and a stream S7 depleted of formaldehyde compared to S6,
where the melting in (b-3) comprises:
(b-3.1) melting a portion, preferably from 0.1% to 5% by weight, further preferably from 0.5% to 3% by weight, of the solid crystallized acetic acid separated in (b-2),
(b-3.2) separating the acetic acid melted in (b-3.1) from the non-molten acetic acid,
(b-3.3) melting the non-molten acetic acid obtained in (b-3.2), preferably by heating to a temperature in the range from 10 to 30° C., preferably from 15 to 20° C., to obtain stream S9,
and where stream S10 is at least partly recycled into the process of the invention.
Crystallizing in (d-1), separating in (d-2) and melting in (d-3)

Preferably, the stream S11 which is enriched in acrylic acid compared to S8 and is obtained in (c) is sent to a crystallization. The process of the invention therefore preferably additionally comprises
(d-1) crystallizing at least a portion of the acrylic acid present in S11 to obtain solid crystallized acrylic acid in its mother liquor.

In step (d-1) of the process of the invention, at least a portion of the acrylic acid present in stream S11 is crystallized to obtain solid crystallized acrylic acid in its mother liquor. The crystallizing can be effected in continuous or batchwise mode. In addition, it is possible in principle to use any method for crystallization known to the person skilled in the art, such as cooling crystallization, evaporation crystallization and vacuum crystallization. Preferably, in the context of the present process, the crystallization is effected by cooling crystallization, i.e. by lowering the temperature of stream S11 in continuous mode, or of a withdrawn fraction of stream S11 in batchwise mode.

The liquid stream S11 may in principle be at any temperature suitable for the present process. Preferably, stream S11 is at a temperature in the range from 20 to 80° C., further preferably from 25 to 60° C., further preferably from 30 to 50° C., further preferably from 35 to 45° C., further preferably from 38 to 42° C.

Preferably, in the context of the present process, the mother liquor obtained in (d-1) is separated from the solid crystallized acrylic acid. Preferably, the present process therefore additionally comprises
(d-2) separating the mother liquor from the acrylic acid crystallized in (d-1) to obtain the solid crystallized acrylic acid and a liquid stream S13.

With regard to the crystallization, seed crystal formation, melting, washing and sweating, and also separating, the descriptions given for the crystallizing in (b-1) and separating in (b-2) apply analogously.

In the case of a suspension crystallization, the at least a portion of stream S11 is cooled preferably to an end temperature in the range from −25 to 15° C., further preferably from 0 to 13° C., further preferably from 7 to 11° C. Preferably, the solids content of the suspension obtained at the end temperature is in the range from 10% to 50% by weight, preferably from 20% to 40% by weight, further preferably from 25% to 35% by weight, based in each case on the at least one portion of stream S11.

The mother liquor separated in (d-2), preferably by means of a centrifuge, as stream S13 is not restricted in terms of the further use thereof. Thus, stream S13 can be removed from the process of the invention or, optionally after one or more workups, fed back to the process of the invention. Preferably, stream S13, optionally after one or more workups, is at least partly recycled into the process of the invention. Further preferably, stream S13, optionally after one or more workups, is recycled into the process of the invention to an extent of at least 90% by weight, further preferably to an extent of at least 95% by weight, further preferably to an extent of at least 99% by weight. Further preferably, stream S13, optionally after one or more workups, is at least partly recycled into the column in (c), preferably to an extent of at least 90% by weight, further preferably to an extent of at least 95% by weight, further preferably to an extent of at least 99% by weight, preferably at a temperature in the range from 50 to 90° C., further preferably from 65 to 75° C. Further preferably, stream S13, optionally after one or more workups, is at least partly recycled into the column in (c), preferably to an extent of at least 90% by weight, further preferably to an extent of at least 95% by weight, further preferably to an extent of at least 99% by weight, preferably at a temperature in the range from 50 to 90° C., further preferably from 65 to 75° C., to the 2nd theoretical plate.

In principle, the solid crystallized acrylic acid crystallized in (d-1) and preferably separated in (d-2) can be sent to the further use thereof in the solid or liquid state, optionally after one or more workup steps which follow on from (d-2).

Preferably, the solid crystallized acrylic acid crystallized in (d-1) and preferably separated in (d-2) is sent to further use thereof in the liquid state. It is preferable here that the solid crystallized acrylic acid separated in (d-2), optionally after one or more workup steps which follow on from (d-2), is melted by heating to obtain a stream S14.

The temperature to which the solid crystallized acrylic acid separated in (d-2) is heated for melting may in principle assume any value which is above the melting point of acrylic acid but at which no breakdown or polymerization or oligomerization of the acrylic acid takes place. If the acrylic acid comprises impurities, which may lead to the formation of a eutectic mixture, it is equally possible in the context of the present process that a temperature below the melting point of pure acrylic acid will be sufficient to melt the solid crystallized acrylic acid separated in (d-2) and hence to convert it to the liquid state. Preferably, the solid crystallized acrylic acid separated in (d-2), for melting is heated to a temperature in the range from 5 to 50° C., preferably from 10 to 30° C., to obtain a stream S14.

Preferably, the process of the invention therefore additionally comprises (d-3) optionally after one or more workup steps which follow on from (d-2), melting the solid crystallized acrylic acid separated in (d-2), preferably by heating to a temperature in the range from 5 to 50° C., preferably from 10 to 30° C., to obtain a stream S14.

In order to increase the acrylic acid content of stream S14, the melting in (d-3) is preferably conducted in such a way that the solid crystallized acrylic acid separated in (d-2) is partly melted and this molten acrylic acid is separated from the non-molten acrylic acid, before the remaining non-molten acrylic acid is melted to obtain stream S14. Preferably, the melting in (d-3) therefore additionally comprises (d-3.1) melting a portion, preferably from 0.1% to 5% by weight, further preferably from 0.5% to 3% by weight, of the solid crystallized acrylic acid separated in (b-2), (d-3.2) separating the acrylic acid melted in (b-3.1) from the non-molten acrylic acid, (d-3.3) melting the non-molten acrylic acid obtained in (b-3.2), preferably by heating to a temperature in the range from 5 to 50° C., preferably from 10 to 30° C., to obtain stream S14.

Stream S14 preferably comprises at least 92% by weight of acrylic acid, further preferably at least 95% by weight, further preferably at least 97% by weight, further preferably at least 98% by weight, further preferably at least 99% by weight, further preferably at least 99.7% by weight.

The present invention therefore also relates to a process for obtaining acrylic acid, comprising (a) providing a liquid stream S7 comprising acetic acid and acrylic acid, where the molar ratio of acetic acid to acrylic acid in stream S7 is greater than 1:1, (b-1) crystallizing a portion of the acetic acid present in stream S7 to obtain solid crystallized acetic acid in its mother liquor, (b-2) separating the mother liquor from the acetic acid crystallized in (b-1) to obtain the solid crystallized acetic acid and a liquid stream S8 comprising acrylic acid and acetic acid, (b-3) optionally after one or more workup steps which follow on from (b-2), melting the solid crystallized acetic acid separated in (b-2), preferably by heating to a temperature in the range from 10 to 30° C., preferably from 15 to 20° C., to obtain a stream S9, (c) separating stream S8 into at least one stream S10 depleted of acrylic acid compared to S8 and a stream S11 enriched in acrylic acid compared to S8, (d-1) crystallizing at least a portion of the acrylic acid present in S11 to obtain solid crystallized acrylic acid in its mother liquor, (d-2) separating the mother liquor from the acrylic acid crystallized in (d-1) to obtain the solid crystallized acrylic acid and a liquid stream S13, (d-3) optionally after one or more workup steps which follow on from (d-2), melting the solid crystallized acrylic acid separated in (d-2), preferably by heating to a temperature in the range from 5 to 50° C., preferably from 10 to 30° C., to obtain a stream S14, where the providing of the liquid stream S7 in (a) comprises:

(a-1) providing a gaseous stream S3 comprising acetic acid, formaldehyde and optionally inert gas, (a-2) contacting stream S3 with an aldol condensation catalyst to obtain a stream S4 comprising acetic acid and acrylic acid, preferably acetic acid, acrylic acid, water and formaldehyde, (a-3) separating stream S4 to obtain a stream S5 comprising inert gas and a stream S6 comprising acetic acid and acrylic acid, or comprising acetic acid, acrylic acid, water, formaldehyde and any formic acid, (a-4) separating stream S6 to obtain a stream S15 enriched in formaldehyde compared to S6 and a stream S7 depleted of formaldehyde compared to S6.

The present invention therefore also further relates to a process for obtaining acrylic acid, comprising (a) providing a liquid stream S7 comprising acetic acid and acrylic acid, where the molar ratio of acetic acid to acrylic acid in stream S7 is greater than 1:1, (b-1) crystallizing a portion of the acetic acid present in stream S7 to obtain solid crystallized acetic acid in its mother liquor, (b-2) separating the mother liquor from the acetic acid crystallized in (b-1) to obtain the solid crystallized acetic acid and a liquid stream S8 comprising acrylic acid and acetic acid, (b-3) optionally after one or more workup steps which follow on from (b-2), melting the solid crystallized acetic acid separated in (b-2), preferably by heating to a temperature in the range from 10 to 30° C., preferably from 15 to 20° C., to obtain a stream S9, (c) separating stream S8 into at least one stream S10 depleted of acrylic acid compared to S8 and a stream S11 enriched in acrylic acid compared to S8, (d-1) crystallizing at least a portion of the acrylic acid present in stream S11 to obtain solid crystallized acrylic acid in its mother liquor, (d-2) separating the mother liquor from the acrylic acid crystallized in (d-1) to obtain the solid crystallized acrylic acid and a liquid stream S13, (d-3) optionally after one or more workup steps which follow on from (d-2), melting the solid crystallized acrylic acid separated in (d-2), preferably by heating to a temperature in the range from 5 to 50° C., preferably from 10 to 30° C., to obtain a stream S14, where the providing of the liquid stream S7 in (a) comprises:

(a-1) providing a gaseous stream S3 comprising acetic acid, formaldehyde and optionally inert gas, (a-2) contacting stream S3 with an aldol condensation catalyst to obtain a stream S4 comprising acetic acid and acrylic acid, preferably acetic acid, acrylic acid, water and formaldehyde, (a-3) separating stream S4 to obtain a stream S5 comprising inert gas and a stream S6 comprising acetic acid and acrylic acid, or comprising acetic acid, acrylic acid, water, formaldehyde and any formic acid, (a-4) separating stream S6 to obtain a stream S15 enriched in formaldehyde compared to S6 and a stream S7 depleted of formaldehyde compared to S6, where the melting in (b-3) comprises:
(b-3.1) melting a portion, preferably from 0.1% to 5% by weight, further preferably from 0.5% to 3% by weight, of the solid crystallized acetic acid separated in (b-2),
(b-3.2) separating the acetic acid melted in (b-3.1) from the non-molten acetic acid,
(b-3.3) melting the non-molten acetic acid obtained in (b-3.2), preferably by heating to a temperature in the range from 10 to 30° C., preferably from 15 to 20° C., to obtain stream S9,
and where stream S10 is at least partly recycled into the process of the invention.

Separating in (e)

Stream S15a is not restricted in terms of the further use thereof. Preferably, stream S15a is subjected to at least one workup, preferably at least for separation, further preferably at least one rectificative separation, and at least partly recycled into the present process at a suitable point. The present process therefore preferably additionally comprises
(e) separating stream S15a, obtained from stream S15, to obtain a stream S16 and a stream S17.

The present invention therefore also relates to a process for obtaining acrylic acid, comprising
(a) providing a liquid stream S7 comprising acetic acid and acrylic acid, where the molar ratio of acetic acid to acrylic acid in stream S7 is greater than 1:1,
(b-1) crystallizing a portion of the acetic acid present in stream S7 to obtain solid crystallized acetic acid in its mother liquor,
(b-2) separating the mother liquor from the acetic acid crystallized in (b-1) to obtain the solid crystallized acetic acid and a liquid stream S8 comprising acrylic acid and acetic acid,
(b-3) optionally after one or more workup steps which follow on from (b-2), melting the solid crystallized acetic acid separated in (b-2), preferably by heating to a temperature in the range from 10 to 30° C., preferably from 15 to 20° C., to obtain a stream S9,
(c) separating stream S8 into at least one stream S10 depleted of acrylic acid compared to S8 and a stream S11 enriched in acrylic acid compared to S8,
(d-1) crystallizing at least a portion of the acrylic acid present in stream S11 to obtain solid crystallized acrylic acid in its mother liquor,
(d-2) separating the mother liquor from the acrylic acid crystallized in (d-1) to obtain the solid crystallized acrylic acid and a liquid stream S13,
(d-3) optionally after one or more workup steps which follow on from (d-2), melting the solid crystallized acrylic acid separated in (d-2), preferably by heating to a temperature in the range from 5 to 50° C., preferably from 10 to 30° C., to obtain a stream S14,
(e) separating stream S15a, obtained from stream S15, to obtain a stream S16 and a stream S17,
where the providing of the liquid stream S7 in (a) comprises:
(a-1) providing a gaseous stream S3 comprising acetic acid, formaldehyde and optionally inert gas,
(a-2) contacting stream S3 with an aldol condensation catalyst to obtain a stream S4 comprising acetic acid and acrylic acid, preferably acetic acid, acrylic acid, water and formaldehyde,
(a-3) separating stream S4 to obtain a stream S5 comprising inert gas and a stream S6 comprising acetic acid and acrylic acid, or comprising acetic acid, acrylic acid, water, formaldehyde and any formic acid,
(a-4) separating stream S6 to obtain a stream S15 enriched in formaldehyde compared to S6 and a stream S7 depleted of formaldehyde compared to S6.

Preferably, stream S15a is separated in the column in (e) into at least two, preferably into two, streams, in which case preferably at least one of the streams thus obtained is at least partly recycled into the present process.

Preferably, stream S15a is separated to obtain a stream S17 enriched in formaldehyde compared to S15a and a stream S16 depleted of formaldehyde compared to S15a.

With regard to the separating in (e), this can be effected by any suitable method or combination of methods known to the person skilled in the art. Preferably, the separating in (e) is effected by rectification. For rectificative separation, it is possible in principle to use any suitable apparatus or any suitable combination of apparatuses. Preference is given here to using at least one column, further preferably one or two columns, further preferably one column, having separating internals in accordance with the invention. Particular preference is given to using a column operated as a rectification column having separating internals. More preferably, the column in (e) is a column having random packings.

In principle, the at least one column for the separating in (e) is not restricted in terms of theoretical plates, provided that the described separating in (e) is achieved. Preferably, the at least one column operated by rectificative means has 10 to 40, further preferably 20 to 30, further preferably 23 to 27, theoretical plates.

In principle, stream S15a can be fed in in the stripping section of the column or in the rectifying section of the column. Preferably, stream S15a is fed to the column in (c) in the region between the 5th and 10th theoretical plates, preferably to the 7th theoretical plate, preferably via a liquid distributor.

In principle, the separating in (e) can be effected at any suitable pressure. Preferably, the separating in (e) is effected at a pressure at the top of the column in the range from 0.01 to 1.0 bar, further preferably 0.05 to 0.5 bar, further preferably 0.08 to 0.12 bar.

Equally, the separating in (e) can in principle be effected at any suitable temperature. Preferably, the separating in (e) is effected at a temperature in the bottom of the column in the range from 30 to 100° C., further preferably from 50 to 80° C., further preferably from 60 to 70° C.

Preferably, the separating in (e) is conducted at a pressure at the top of the column in the range from 0.01 to 1.0 bar, further preferably 0.05 to 0.5 bar, further preferably 0.08 to 0.12 bar, and at the same time, for each of the pressure ranges mentioned, at a temperature in the bottom of the column in the range from 30 to 100° C., further preferably from 50 to 80° C., further preferably from 60 to 70° C.

In principle, stream S16 can be withdrawn in the rectifying section of the column or from the top of the column. Preferably, stream S16 is withdrawn from the top of the column.

Preferably, stream S16 is condensed virtually completely in a shell and tube apparatus and partly recycled into the column in (e) via a liquid distributor above the uppermost bed of random packings as a liquid return stream as S16b, and the remaining portion of the condensate is removed from the process as wastewater as stream S16a. The uncondensed portion is preferably removed from the process as offgas as stream S21.

In principle, stream S17 can be withdrawn in the stripping section of the column or from the bottom of the column. Preferably, stream S17 is withdrawn from the bottom of the column in (e).

The bottom stream of the column in (e), stream S17, containing the aqueous formaldehyde solution enriched in formaldehyde compared to S15a, is not restricted in principle in terms of the further use thereof. Thus, stream S17 can be removed from the process of the invention or, optionally after one or more workups, fed back to the process of the invention. Preferably, stream S17, optionally after one or more workups, is at least partly recycled into the process of the invention. Further preferably, stream S17, optionally after one or more workups, is recycled into the process of the invention to an extent of at least 90% by weight, further preferably to an extent of at least 95% by weight, further preferably to an extent of at least 99% by weight.

Stream S17 comprises an aqueous formaldehyde solution enriched in formaldehyde compared to S15 and may comprise at least one further component, the at least one further component preferably being selected from the group consisting of acetic acid, acrylic acid, methanol, formic acid, propionic acid, acetone, acetaldehyde, acrolein, methyl acetate, methyl acrylate and methacrolein. Preferably, stream S17 consists of water and formaldehyde to an extent of 50% to 99% by weight, further preferably to an extent of 60% to 90% by weight, further preferably to an extent of 65% to 80% by weight or 68% to 72% by weight or 78% to 82% by weight.

Evaporative Concentration in (a-0)

Stream S17 may be recycled at least partly into the process of the invention, in principle at any suitable point. For example, it is possible to recycle stream S17 into step (a-1). It is likewise possible to feed stream S17 at least partly to an evaporative concentration stage (a-0) together with at least one further formaldehyde-containing stream S0 before feeding it to (a-1) By evaporative concentration, which is conducted in a helical tube evaporator or a thin-film evaporator for example, it is possible to establish the desired water content of a resulting formaldehyde-containing stream S1. Preferably, the present process therefore additionally comprises (a-0) feeding stream S17 at least partly and a further formaldehyde-containing stream S0 to an evaporative concentration stage to obtain the desired water content in the resulting formaldehyde-containing stream S1 and a water-containing stream Opt1.

The mass ratio of water based on formaldehyde in stream S1 is preferably in the range from 3:1 to 0.1:1, further preferably in the range from 2:1 to 0.5:1, further preferably in the range from 1.5:1 to 0.75:1.

The water-containing stream Opt1 is not restricted in terms of the further use thereof. For example, it is possible that stream Opt1 is removed from the process. It is equally possible that stream Opt1 is fed to the present process at a suitable point. Preferably, stream Opt1, optionally after one or more workups, is at least partly fed to the column in (e), preferably to an extent of at least 90% by weight, further preferably to an extent of at least 95% by weight, further preferably to an extent of at least 99% by weight.

In principle, stream S3 can be provided in (a-1) by contacting any number of different streams. Thus, it is possible to provide stream S3 by contacting at least one formaldehyde-containing stream and at least one acetic acid-containing stream. Preferably, stream S3 is provided in (a-1) by contacting a formaldehyde-containing stream S1, an acetic acid-containing stream S2, a recycled acetic acid-containing stream S9, an inert gas-containing, preferably nitrogen-containing, stream S18, and an oxygen-containing stream S19, and optionally co-evaporation. It is likewise possible to evaporate the streams individually or combinations of two or more thereof, and then to contact them with one another. Useful evaporators include all suitable evaporators known to those skilled in the art, for example falling-film evaporators, natural circulation evaporators, shell and tube evaporators, forced circulation evaporators and thin-film evaporators.

The inert gas-containing stream S18 consists of inert gas preferably to an extent of at least 75% by weight, further preferably at least 80% by weight, further preferably at least 90% by weight. Further preferably, the inert gas-containing stream S18 consists of nitrogen to an extent of at least 75% by weight, further preferably at least 80% by weight, further preferably at least 90% by weight.

The oxygen-containing stream S19 consists of oxygen preferably to an extent of at least 5% by weight, further preferably at least 10% by weight. Oxygen sources used here may be oxygen or air or a mixture thereof.

The stream S2 which serves as acetic acid source consists of acetic acid preferably to an extent of at least 80% by weight, further preferably at least 90% by weight, further preferably at least 95% by weight, further preferably at least 98% by weight.

The stream S0 which serves as formaldehyde source consists of formaldehyde preferably to an extent of at least 25% by weight, further preferably of at least 35% by weight, further preferably of at least 45% by weight.

The present invention is illustrated in detail by the following embodiments and combinations of embodiments which are apparent from the corresponding dependency references and other references:

1. A process for obtaining acrylic acid, comprising
   (a) providing a liquid stream S7 comprising acetic acid and acrylic acid, where the molar ratio of acetic acid to acrylic acid in stream S7 is greater than 1:1,
   (b-1) crystallizing a portion of the acetic acid present in stream S7 to obtain solid crystallized acetic acid in its mother liquor,
   (b-2) separating the mother liquor from the acetic acid crystallized in (b-1) to obtain the solid crystallized acetic acid and a liquid stream S8 comprising acrylic acid and acetic acid,
   (c) separating stream S8 into at least one stream S10 depleted of acrylic acid compared to S8 and a stream S11 enriched in acrylic acid compared to S8.
2. The process according to embodiment 1, wherein the molar ratio of acetic acid to acrylic acid in stream S7 is in the range from 1.1:1 to 20:1, preferably in the range from 2:1 to 15:1, further preferably in the range from 3:1 to 10:1.
3. The process according to embodiment 1 or 2, wherein stream S7 consists of acetic acid and acrylic acid to an extent of 45% to 100% by weight, preferably to an extent of 65% to 99.9% by weight, further preferably to an extent of 85% to 99.8% by weight, further preferably to an extent of 98% to 99.7% by weight.
4. The process according to embodiment 1 or 2, wherein stream S7 consists of acetic acid, acrylic acid, water, formaldehyde and any formic acid to an extent of 45% to 100% by weight, preferably to an extent of 65% to 99.9% by weight, further preferably to an extent of 85% to 99.8% by weight, further preferably to an extent of 98% to 99.7% by weight.
5. The process according to any of embodiments 1 to 4, wherein stream S7 is at a temperature in the range from 20 to 80° C., preferably from 25 to 60° C., further preferably from 35 to 45° C.

6. The process according to any of embodiments 1 to 5, wherein the acetic acid content of stream S8 is in the range from 1% to 95% by weight, preferably from 25% to 93% by weight, further preferably from 50% to 90% by weight.
7. The process according to any of embodiments 1 to 6, wherein the separating in (b-2) is effected by means of centrifuging, filtering, decanting, spray-drying, pumping off, or a combination of two or more thereof, preferably by means of centrifuging, filtering or a combination thereof.
8. The process according to any of embodiments 1 to 7, wherein the separating in (b-2) comprises washing the solid crystallized acetic acid with one or more washing compositions, preferably comprising acetic acid, preferably with acetic acid.
9. The process according to any of embodiments 1 to 8, wherein the separating in (b-2) additionally comprises the drying of the solid crystallized acetic acid.
10. The process according to any of embodiments 1 to 9, wherein the sequence (b-1) (b-2) is conducted at least once, preferably once.
11. The process according to any of embodiments 1 to 10, additionally comprising
    (b-3) optionally after one or more workup steps which follow on from (b-2), melting the solid crystallized acetic acid separated in (b-2), preferably by heating to a temperature in the range from 10 to 30° C., preferably from 15 to 20° C., to obtain a stream S9.
12. The process according to embodiment 11, wherein the melting in (b-3) comprises:
    (b-3.1) melting a portion, preferably from 0.1% to 5% by weight, further preferably from 0.5% to 3% by weight, of the solid crystallized acetic acid separated in (b-2),
    (b-3.2) separating the acetic acid melted in (b-3.1) from the non-molten acetic acid,
    (b-3.3) melting the non-molten acetic acid obtained in (b-3.2), preferably by heating to a temperature in the range from 10 to 30° C., preferably from 15 to 20° C., to obtain stream S9.
13. The process according to embodiment 11 or 12, wherein the acetic acid content of stream S9 is from 80% to 99.999% by weight, preferably from 85% to 99% by weight, further preferably from 90% to 98.5% by weight.
14. The process according to any of embodiments 11 to 13, wherein stream S9, optionally after one or more workups, is at least partly recycled into the process for obtaining acrylic acid, preferably to an extent of 50% to 100% by weight, further preferably to an extent of 75% to 100% by weight, further preferably to an extent of 95% to 100% by weight.
15. The process according to any of embodiments 1 to 14, wherein the crystallizing in (b-1) is effected by means of layer crystallization on at least one heat exchanger surface.
16. The process according to embodiment 15, wherein the at least one heat exchange surface is at a temperature in the range from −35 to +16.5° C., preferably in the range from −30 to +10° C., further preferably in the range from −25 to +5° C.
17. The process according to any of embodiments 1 to 14, wherein the crystallizing in (b-1) is effected by means of suspension crystallization to obtain a suspension comprising solid crystallized acetic acid.
18. The process according to embodiment 17, wherein crystallization is accomplished by cooling at least a portion of stream S7 down to an end temperature in the range from −35 to +17° C., preferably from −25 to +12° C., further preferably from −20 to +10° C.
19. The process according to embodiment 18, wherein the cooling rate of the at least one portion of stream S7 is in the range from 0.1 to 5 K/h, preferably from 0.5 to 2.5 K/h, further preferably from 0.7 to 1.3 K/h.
20. The process according to embodiment 18 or 19, wherein the solids content of the suspension obtained at the end temperature is in the range from 10% to 50% by weight, preferably from 20% to 40% by weight, further preferably from 25% to 35% by weight, based in each case on the at least one portion of stream S7.
21. The process according to any of embodiments 1 to 20, wherein the separation in (c) is effected by rectificative means, preferably using at least one column, further preferably one or two columns, further preferably one column, equipped with separating internals.
22. The process according to embodiment 21, wherein the rectificative column has 5 to 40, preferably 11 to 15, theoretical plates.
23. The process according to either of embodiments 21 and 22, wherein the separating in (c) is effected at a pressure at the top of the column in the range from 0.01 to 0.5 bar, preferably in the range from 0.02 to 0.08 bar, further preferably in the range from 0.04 to 0.06 bar.
24. The process according to any of embodiments 21 to 23, wherein the separating in (c) is effected at a temperature in the bottom of the column in the range from 60 to 105° C., preferably in the range from 70 to 95° C., further preferably in the range from 80 to 85° C.
25. The process according to any of embodiments 21 to 24, wherein stream S10 is withdrawn from the top of the column in (c).
26. The process according to any of embodiments 1 to 25, wherein stream S7 comes from an aldol condensation, preferably from an aldol condensation and one or more subsequent workups.
27. The process according to any of embodiments 1 to 26, wherein the providing of the liquid stream S7 in (a) comprises:
    (a-1) providing a gaseous stream S3 comprising acetic acid, formaldehyde and optionally inert gas,
    (a-2) contacting stream S3 with an aldol condensation catalyst to obtain a stream S4 comprising acetic acid and acrylic acid, preferably acetic acid, acrylic acid, water and formaldehyde,
    (a-3) optionally separating stream S4 to obtain a stream S5 comprising inert gas and a stream S6 comprising acetic acid and acrylic acid, or comprising acetic acid, acrylic acid, water, formaldehyde and any formic acid,
    (a-4) optionally separating stream S6 to obtain a stream S15 enriched in formaldehyde compared to S6 and a stream S7 depleted of formaldehyde compared to S6,
    where, if (a-3) is not conducted and (a-4) is conducted, S4 is the same as S6;
    where, if (a-4) is not conducted and (a-3) is conducted, S6 is the same as S7;
    where, if neither (a-3) nor (a-4) is conducted, S4 is the same as S7.
28. The process according to embodiment 27, wherein the molar ratio of acetic acid to formaldehyde in stream S3 is greater than 1:1 and preferably in the range from 1.1:1 to 10:1, further preferably from 1.5:1 to 8:1, further preferably from 1.9:1 to 4.1:1.
29. The process according to embodiment 27 or 28, wherein stream S3 additionally comprises water, or inert gas, or water and inert gas.

30. The process according to any of embodiments 27 to 29, wherein stream S3 consists of acetic acid, formaldehyde, water and inert gas to an extent of 50% to 99% by weight, preferably to an extent of 70% to 99.5% by weight, further preferably to an extent of 85% to 99% by weight.
31. The process according to any of embodiments 27 to 30, comprising
    (b-3) optionally after one or more workup steps which follow on from (b-2), melting the solid crystallized acetic acid separated in (b-2), preferably by heating to a temperature in the range from 10 to 30° C., preferably from 15 to 20° C., to obtain a stream S9,
    where stream S9 is at least partly recycled into (a-1), preferably to an extent of 50% to 100% by weight, further preferably to an extent of 75% to 100% by weight, further preferably to an extent of 95% to 100% by weight.
32. The process according to any of embodiments 27 to 31, wherein the separating in (a-3) comprises the cooling of stream S4 to a temperature in the range from −33 to 160° C. and the condensing of at least a portion of stream S4 to obtain a gaseous stream S5 and a liquid stream S6.
33. The process according to any of embodiments 27 to 32, wherein the gaseous stream S5, optionally after one or more workups, is at least partly recycled into the process, preferably to an extent of 10% to 100% by weight, further preferably to an extent of 20% to 70% by weight, further preferably to an extent of 25% to 45% by weight.
34. The process according to embodiment 33, wherein stream S5 is at least partly recycled into (a-1) as stream Opt2, preferably to an extent of 50% to 100% by weight, further preferably to an extent of 75% to 99% by weight, further preferably to an extent of 80% to 98% by weight.
35. The process according to any of embodiments 27 to 34, wherein the separating in (a-4) is effected by rectificative means, preferably using at least one column, further preferably one or two columns, further preferably one column, preferably equipped with separating internals.
36. The process according to embodiment 35, wherein the column has 25 to 60, preferably 32 to 38, theoretical plates.
37. The process according to either of embodiments 35 and 36, wherein the separating in (a-4) is effected at a pressure at the top of the column in the range from 0.1 to 2 bar, preferably from 0.7 to 1.5 bar, further preferably from 0.9 to 1.3 bar.
38. The process according to any of embodiments 35 to 37, wherein the separating in (a-4) is effected at a temperature in the bottom of the column in the range from 100 to 200° C., preferably in the range from 120 to 140° C.
39. The process according to any of embodiments 35 to 38, wherein a stream S15 is withdrawn from the top of the column in (a-4).
40. The process according to any of embodiments 36 to 39, wherein stream S7 is withdrawn from the bottom of the column in (a-4).
41. The process according to any of embodiments 27 to 40, wherein at least a portion of stream S10 is recycled into the column in (c) as return stream S10b and at least a portion of stream S10 is recycled into the column in (a-4) as stream S10a, where the weight ratio of stream S10b to stream S10a is preferably from 0.1 to 3, further preferably from 0.3 to 1.5, further preferably from 0.5 to 0.7.
42. The process according to embodiment 41, wherein 50% to 100% by weight, further preferably 75% to 99% by weight, further preferably 80% to 98% by weight, of stream S10 is recycled into the column in (a-4) as stream S10a, optionally after one or more workups.
43. The process according to any of embodiments 27 to 42, additionally comprising
    (e) separating stream S15a, obtained from stream S15, to obtain a stream S16 and a stream S17.
44. The process according to any of embodiments 1 to 43, additionally comprising
    (d-1) crystallizing at least a portion of the acrylic acid present in S11 to obtain solid crystallized acrylic acid in its mother liquor.
45. The process according to embodiment 44, additionally comprising
    (d-2) separating the mother liquor from the acrylic acid crystallized in (d-1) to obtain the solid crystallized acrylic acid and a liquid stream S13.
46. The process according to embodiment 45, wherein stream S13, optionally after one or more workups, is at least partly recycled into the column in (c), preferably to an extent of at least 90% by weight, further preferably to an extent of at least 95% by weight, further preferably to an extent of at least 99% by weight.

U.S. Provisional Patent Application No. 62/086,753, filed 3 Dec. 2014, is incorporated into the present application by literature reference. With regard to the abovementioned teachings, numerous changes and deviations from the present invention are possible. It can therefore be assumed that the invention, within the scope of the appended claims, can be performed differently from the way described specifically herein.

BRIEF DESCRIPTION OF THE FIGURES

FIG. 1 shows the flow diagram of a preferred configuration of the process of the invention, comprising stages (a-0), (a-1), (a-2), (a-3), (a-4), (b-1), (b-2), (b-3), (c), (d-1), (d-2) and (e), as described above. The streams S1 to S21 and Opt1 to Opt4 shown in FIG. 1, and the stages and apparatuses depicted, are elucidated in detail above and in example 2.

The present invention is illustrated further by the examples which follow.

EXAMPLES

I. Analysis

I.1 Determination of Water Content

For the titrimetric determination of the water content according to Karl Fischer, the titrant used was Hydranal® Composite 5K and the working medium Hydranal® Medium K (+ about 10 mL of Hydranal® Buffer Acid) (each from Sigma-Aldrich).

I.2 Determination of Formaldehyde Content

The formaldehyde content was determined by means of titration by the sulfite method, by reaction of formaldehyde with sodium sulfite and titration of the sodium hydroxide released with sulfuric acid. To obtain the neutralized sodium sulfite solution, 126 g of sodium sulfite (1 mol) were made up to 1 L with distilled water, dissolved and adjusted to a pale blue color with 1 M aqueous sodium hydroxide solution against thymolphthalein (0.1% in methanol; 8-10 drops). To determine the formaldehyde content of a sample, a 100 mL Erlenmeyer flask was initially charged with 5 mL of distilled water, and about 10 g of the sample were weighed in; in the case of high expected contents of formaldehyde, a correspondingly smaller amount was weighed in. Thymolphthalein (0.1% in methanol; 5 drops) was added, and the solution was neutralized with 0.1 M sodium hydroxide solution or with 0.05 M sulfuric acid according to the color. Then 40 mL of the neutralized sodium sulfite solution were added, and the resultant blue color was titrated with 0.5 M sulfuric acid as far as a pale blue shade corresponding to the pale blue color of the neutralized sodium sulfite solution. 1 mL of 0.5 M sulfuric acid thus corresponds to 0.03002 g of formaldehyde.

1.3 Gas Chromatography

For gas chromatography, an instrument of the Agilent 7890 type with an FFAP column was used. The temperature program was selected as follows:
- hold at 40° C. for 10 min;
- heat to 90° C. at a heating rate of 2 K/min;
- heat to 200° C. at a heating rate of 6 K/min;
- heat to 250° C. at a heating rate of 25 K/min;
- hold at 250° C. for 10 min.

II.1 Example 1

A mixture according to table 1 comprising acetic acid (Bernd Kraft, >99%) and acrylic acid (BASF, >99%), and also optionally formaldehyde (BASF, 49% by weight aqueous solution) and optionally water, was introduced at atmospheric pressure into a 3 liter jacketed stirred vessel (diameter: 150 mm) having a close-clearance helical stirrer. Thereafter, the mixture was cooled from 10° C. at a cooling rate of 1 K/h down to the end temperature specified in each case. The temperature was measured in the mixture with a Pt100 thermocouple. In the course of cooling, crystals formed in the mixture, which were kept in suspension by stirring at 150 rpm (revolutions per minute) to 250 rpm. The resultant crystals in the suspension were removed with a drum centrifuge at 2000 rpm within 1 min. The solids content obtained at the end temperature in each case is reported in table 1.

The formaldehyde and water content in the solids and the mother liquor was determined according to I.1 and I.2 (see above under "Analysis"), and the proportions of acetic acid and acrylic acid by means of gas chromatography (see above under "Analysis", I.3). The results are shown in tables 2-4 below. As a result of the different analytical methods used, it is possible that the proportions of the components of a mixture do not add up to 100% by weight.

TABLE 1

Compositions and amounts of mixtures 1-5 used and the corresponding melting temperature, end temperature and resulting solids content after one-stage crystallization

| Mixture | 1 | 2 | 3 | 4 | 5 |
|---|---|---|---|---|---|
| Total amount/g | 500 | 500 | 2400 | 2400 | 2400 |
| Acetic acid/% by weight | 68 | 82 | 73 | 83 | 90 |
| Acrylic acid/% by weight | 13 | 7.5 | 27 | 17 | 10 |
| Formaldehyde/% by weight | 4 | 2.5 | — | — | — |
| Water/% by weight | 15 | 8 | — | — | — |
| Melting point/° C. | −10 to −11 | 0 to −1 | 1 | 7 | 11 |
| End temperature/° C. | −18 | −10.5 | −11 | −1.7 | 9.5 |
| Solids content/% by weight | 6.3 | 12.3 | 29.8 | 34.8 | 36.9 |

TABLE 2

Composition of the mother liquor

| Mixture | 1 | 2 | 3 | 4 | 5 |
|---|---|---|---|---|---|
| Acetic acid/% by weight | 64.6 | 78.0 | 60.6 | 73.9 | 79.1 |
| Acrylic acid/% by weight | 13.5 | 9.2 | 39.4 | 24.4 | 19.3 |
| Formaldehyde/% by weight | 4.6 | 3.5 | — | — | — |
| Water/% by weight | 15.7 | 9.3 | — | — | — |

TABLE 3

Composition of the crystals

| Mixture | 1 | 2 | 3 | 4 | 5 |
|---|---|---|---|---|---|
| Acetic acid/% by weight | 94.1 | 97.2 | 94.3 | 97.3 | 96.8 |
| Acrylic acid/% by weight | 2.2 | 1.0 | 5.3 | 2.4 | 2.1 |
| Formaldehyde/% by weight | 0.7 | 0.4 | — | — | — |
| Water/% by weight | 2.7 | 1.3 | — | — | — |

TABLE 4

Yield of acetic acid after one-stage crystallization and partition coefficients for acrylic acid and any formaldehyde and water

| Mixture | 1 | 2 | 3 | 4 | 5 |
|---|---|---|---|---|---|
| Yield of acetic acid/% | 9 | 15 | 38 | 41 | 40 |
| Partition coefficient of acrylic acid | 0.167 | 0.105 | 0.133 | 0.100 | 0.110 |
| Partition coefficient of formaldehyde | 0.154 | 0.119 | — | — | — |
| Partition coefficient of water | 0.174 | 0.137 | — | — | — |

The results shown in table 3 show that, proceeding from the illustrative mixtures 1-5, it is possible to obtain solid crystallized acetic acid in high purity by crystallization.

II.2 Example 2

The example which follows was run with the aid of the process simulation program CHEMASIM from BASF. The calculated streams S0 to S21 are shown in tables 5.1-5.4 and tables 6.1-6.4 for a molar ratio of acetic acid to formaldehyde in stream S3 of 2:1 and 4:1 respectively. In these tables, "E" represents 10^x, i.e. $1.00E-01=10^{-1}=0.100$, "L" represents liquid and "G" represents gaseous. By way of example, a product capacity of 1 t of acrylic acid/h was fixed.

For mass balance reasons, an additional oxygen source is listed for step (a-2). As a result of rounding of the values in tables 5.1-5.4 and tables 6.1-6.4, it is possible that the individual components specified for a stream do not add up to 100% by weight.

II.2.1 Steps (a-0) and (a-1)

Fresh aqueous formaldehyde (S0) and aqueous formaldehyde from the recycling (S17) are combined (a-0) to obtain stream S1. Stream S1, fresh acetic acid (S2), acetic acid from the recycling (S9), fresh nitrogen (S18) and fresh air (S19) are combined and co-evaporated (a-1) to obtain a stream S3.

II.2.2 Step (a-2)

The stream S3 obtained in (a-1) is contacted with an aldol condensation catalyst comprising V and P and shaped to cylindrical extrudates having a diameter of cross-sectional area of 3 mm and an average extrudate length of 20 mm to obtain a stream S4 (a-2). The reaction is conducted at a temperature of 370° C. and a pressure of 1.1 bar in a shell and tube reactor, the catalytically active fixed bed being within the catalyst tubes, around which fluid heat carrier flows.

II.2.3 Step (a-3)

The gaseous stream S4 obtained in (a-2) is cooled to 0° C. by means of a plurality of heat exchangers and separated to obtain a gaseous stream S5 and a stream S6. The gaseous stream S5 is removed from the process as offgas as stream S5a. The liquid stream S6 is heated and fed in gaseous form to the column in (a-4).

II.2.4 Step (a-4)

The column in (a-4) is configured as a tray column having a number of crossflow trays equivalent to 35 theoretical plates, and is operated in rectificative mode. The feed stream (S6) is fed to the 15th theoretical plate. The vapor from the evaporator which is executed as a shell and tube circulation evaporator and is operated with 4 bar steam is conducted into the column below the first tray. The column in (a-4) is operated at a top pressure of 1.1 bar. The vapors S15 from the column are partly condensed in a shell and tube apparatus, and the liquid component is conducted from there into a distillate vessel and divided into a return stream which is applied to the uppermost tray, and a stream S15a which is fed to process stage (e). The liquid stream S7 at the bottom of the column is cooled by means of a heat exchanger and fed to process stage (b-1).

II.2.5 Steps (b-1) to (b-3)

The liquid stream S7 is cooled to the crystallization temperature in step (b-1). The acetic acid crystals in the suspension obtained, which has a solids content of about 30% by weight, are separated from the mother liquor by means of a centrifuge, melted and fed to process stage (a-1) as stream S9. The mother liquor is heated and fed to stage (c) as stream S8.

II.2.6 Step (c)

The column in (c) is executed as a tray column having a number of dual-flow trays equivalent to 15 theoretical plates, and is operated in rectificative mode. The liquid stream S8 is fed to the column as feed to the 13th theoretical plate. The column is operated under reduced pressure. Above the bottom, the acrylic acid product stream S11 is drawn off in gaseous form and then condensed. High-boiling components such as acrylic acid dimer or oligomers are drawn off in liquid form in the bottom of rectification column (S12). The acetic acid-rich vapors S10 from the column are partly condensed in a shell and tube apparatus. A portion of the condensate is recycled as liquid return stream S10b to the uppermost tray in the column; the other portion is recycled into the column in (a-4) as stream S10a. The uncondensed residue is removed as offgas (S20). The vapor from the evaporator which is executed as a shell and tube circulation evaporator and is operated with 4 bar steam is conducted into the column below the first tray. In addition, the mother liquor S13 recycled from step (d-2) is fed to the column in (c) at the 1st plate.

II.2.7 Steps (d-1) to (d-3)

The liquid stream S11 is cooled to the crystallization temperature of 9° C. in step (d-1). The acrylic acid crystals in the suspension thus obtained, which has a solids content of about 30% by weight, are separated off by means of a centrifuge (d-2) and melted to obtain stream S14 (d-3). The mother liquor S13 is heated to 70° C. and fed to the column in (c).

II.2.8 Step (e)

The stream S15a obtained from the column in (a-4) is fed to the column in (e). The column in (e) is executed as a column with random packings having a bed of random packings of a height equivalent to 15 theoretical plates, and is operated in rectificative mode. The liquid stream S15a is fed to the column as feed to the 5th theoretical plate via a liquid distributor. The return stream from the condenser above the uppermost bed of random packings is fed in via a liquid distributor. The vapor from the evaporator which is executed as a shell and tube circulation evaporator and is operated with 4 bar steam is fed in below the lowermost tray. The column in (e) is operated at a top pressure of 100 mbar, resulting in temperatures of about 46° C. in the top and about 60° C. in the bottom. The vapors S16 from the column are partly condensed in a shell and tube apparatus. A portion of the condensate is recycled as liquid return stream S16b to the uppermost tray in the column; the other portion of the condensate is removed as wastewater as stream S16a. The uncondensed portion is stream S21 removed as offgas. The bottom stream S17 from the column in (e), comprising formaldehyde-enriched aqueous formaldehyde solution, is recycled into (a-0).

TABLE 5.1

Composition of the streams (in g/g of stream) at a molar ratio of acetic acid to formaldehyde in S3 of 2:1

| | Stream | | | | | |
|---|---|---|---|---|---|---|
| | S0 | S1 | S2 | S3 | S4 | S5 |
| State | L | L | L | G | G | G |
| Temperature/° C. | 20 | 53 | 20 | 310 | 370 | 0 |
| Pressure/bar | 1.00 | 1.50 | 1.50 | 1.40 | 1.10 | 1.00 |
| Mass flow rate/kg/h | 1102 | 2225 | 1065 | 8170 | 8276 | 2667 |
| Formaldehyde | 4.90E−01 | 5.31E−1 | — | 1.14E−01 | 4.95E−02 | 8.53E−05 |
| Acetic acid | — | 1.51E−01 | 9.80E−01 | 4.56E−01 | 3.27E−01 | 3.03E−03 |
| Acrylic acid | — | 1.97E−03 | — | 1.22E−02 | 1.33E−01 | 6.27E−04 |
| Water | 4.90E−01 | 3.13E−01 | 2.00E−02 | 1.17E−01 | 1.58E−01 | 2.37E−03 |

TABLE 5.1-continued

Composition of the streams (in g/g of stream) at a molar ratio of acetic acid to formaldehyde in S3 of 2:1

| | Stream | | | | | |
|---|---|---|---|---|---|---|
| | S0 | S1 | S2 | S3 | S4 | S5 |
| Methanol | 2.00E−02 | 2.79E−03 | — | 2.70E−03 | 2.67E−03 | 4.48E−05 |
| Formic acid | 2.50E−04 | 1.25E−04 | — | 3.41E−05 | 3.37E−05 | 2.48E−07 |
| Propionic acid | — | 3.37E−10 | 4.00E−04 | 5.21E−05 | 5.15E−05 | 1.42E−07 |
| Acetone | — | 2.74E−11 | — | 4.05E−09 | 4.32E−04 | 1.24E−04 |
| Acetaldehyde | — | — | — | 4.13E−08 | 1.47E−03 | 1.27E−03 |
| Acrolein | — | 1.77E−12 | — | 1.28E−08 | 9.03E−04 | 3.93E−04 |
| Methyl acetate | — | 1.03E−11 | — | 6.24E−08 | 4.58E−03 | 1.91E−03 |
| Methyl acrylate | — | 8.20E−12 | — | 1.50E−08 | 2.69E−03 | 4.60E−04 |
| Methacrolein | — | 3.33E−09 | — | 1.09E−09 | 5.43E−05 | 5.72E−06 |
| Ethylene | — | — | — | 8.08E−08 | 8.26E−04 | 2.48E−03 |
| Carbon dioxide | — | — | — | 6.49E−05 | 1.64E−02 | 5.10E−02 |
| Oxygen | — | — | — | 2.52E−02 | 2.49E−02 | 7.73E−02 |
| Carbon monoxide | — | — | — | 7.81E−07 | 7.71E−03 | 2.39E−02 |
| Nitrogen | — | — | — | 2.73E−01 | 2.69E−01 | 8.35E−01 |

TABLE 5.2

Composition of the streams at a molar ratio of acetic acid to formaldehyde in S3 of 2:1

| | Stream | | | | | |
|---|---|---|---|---|---|---|
| | S6 | S7 | S8 | S9 | S10a | S11 |
| State | G | L | L | L | L | L |
| Temperature/° C. | 117 | 40 | 69 | 20 | 40 | 40 |
| Pressure/bar | 1.45 | 1.00 | 0.15 | 1.00 | 1.47 | 1.00 |
| Mass flow rate/kg/h | 5609 | 8154 | 5708 | 2446 | 4699 | 3333 |
| Formaldehyde | 7.30E−02 | 5.49E−08 | 7.84E−08 | — | 8.62E−08 | — |
| Acetic acid | 4.82E−01 | 7.66E−01 | 6.83E−01 | 9.60E−01 | 8.27E−01 | 9.20E−03 |
| Acrylic acid | 1.96E−01 | 2.21E−01 | 2.99E−01 | 3.88E−02 | 1.50E−01 | 9.89E−01 |
| Water | 2.32E−01 | 1.60E−03 | 1.81E−03 | 1.10E−03 | 2.19E−03 | 8.76E−11 |
| Methanol | 3.91E−03 | 3.06E−08 | 4.37E−08 | — | 5.28E−08 | — |
| Formic acid | 4.96E−05 | 1.18E−02 | 1.68E−02 | — | 2.04E−02 | 4.01E−09 |
| Propionic acid | 7.58E−05 | 6.92E−05 | 9.89E−05 | — | 2.96E−05 | 1.35E−03 |
| Acetone | 5.78E−04 | 1.05E−11 | 1.50E−11 | — | 1.81E−11 | — |
| Acetaldehyde | 1.57E−03 | — | — | — | — | — |
| Acrolein | 1.15E−03 | 1.44E−12 | 2.06E−12 | — | 2.47E−12 | — |
| Methyl acetate | 5.84E−03 | 1.87E−12 | 2.67E−12 | — | 3.21E−12 | — |
| Methyl acrylate | 3.76E−03 | 1.96E−06 | 2.80E−06 | — | 3.39E−06 | — |
| Methacrolein | 7.74E−05 | 2.65E−08 | 3.79E−08 | — | 4.57E−08 | — |
| Ethylene | 4.14E−05 | — | — | — | — | — |
| Carbon dioxide | — | — | — | — | — | — |
| Oxygen | — | — | — | — | — | — |
| Carbon monoxide | — | — | — | — | — | — |
| Nitrogen | — | — | — | — | — | — |

TABLE 5.3

Composition of the streams at a molar ratio of acetic acid to formaldehyde in S3 of 2:1

| | Stream | | | | | |
|---|---|---|---|---|---|---|
| | S12 | S13 | S14 | S15a | S16a | S17 |
| State | L | L | L | L | L | L |
| Temperature/° C. | 88 | 70 | 25 | 99 | 40 | 60 |
| Pressure/bar | 0.15 | 1.00 | 1.00 | 1.30 | 1.02 | 0.17 |
| Mass flow rate/kg/h | 2 | 2333 | 1000 | 2154 | 893 | 1124 |
| Formaldehyde | — | — | — | 1.90E−01 | 3.67E−05 | 3.49E−01 |
| Acetic acid | 4.62E−03 | 1.23E−02 | 2.00E−03 | 1.60E−01 | 9.86E−03 | 2.99E−01 |
| Acrylic acid | 9.94E−01* | 9.86E−01 | 9.98E−01 | 2.04E−03 | 1.26E−05 | 3.90E−03 |
| Water | 1.77E−11 | 1.25E−10 | 8.76E−13 | 6.04E−01 | 9.40E−01 | 3.49E−01 |
| Methanol | — | — | — | 1.02E−02 | 1.28E−02 | 2.77E−05 |
| Formic acid | 9.98E−10 | 5.73E−09 | — | 1.63E−06 | 2.58E−09 | 3.13E−06 |

TABLE 5.3-continued

Composition of the streams at a molar ratio of acetic acid to formaldehyde in S3 of 2:1

| | Stream | | | | | |
|---|---|---|---|---|---|---|
| | S12 | S13 | S14 | S15a | S16a | S17 |
| Propionic acid | 1.38E−03 | 1.75E−03 | 4.23E−04 | 3.49E−10 | — | 6.68E−10 |
| Acetone | — | — | — | 1.51E−03 | 6.98E−04 | 5.43E−11 |
| Acetaldehyde | — | — | — | 4.10E−03 | 9.58E−04 | 7.80E−13 |
| Acrolein | — | — | — | 2.98E−03 | 6.36E−04 | 3.51E−12 |
| Methyl acetate | — | — | — | 1.52E−02 | 3.09E−03 | 2.04E−11 |
| Methyl acrylate | — | — | — | 9.78E−03 | 1.25E−03 | 1.62E−11 |
| Methacrolein | — | — | — | 2.01E−04 | 2.63E−04 | 6.59E−09 |
| Ethylene | — | — | — | 1.08E−04 | 1.33E−06 | — |
| Carbon dioxide | — | — | — | — | — | — |
| Oxygen | — | — | — | — | — | — |
| Carbon monoxide | — | — | — | — | — | — |
| Nitrogen | — | — | — | — | — | — |

*may also be present in the form of high-boiling acrylic acid adducts, for example dimer and/or oligomer.

TABLE 5.4

Composition of the streams at a molar ratio of acetic acid to formaldehyde in S3 of 2:1

| | Stream | | | |
|---|---|---|---|---|
| | S18 | S19 | S20 | S21 |
| State | G | G | G | G |
| Temperature/° C. | 20 | 20 | 40 | 40 |
| Pressure/bar | 1.50 | 1.50 | 0.07 | 0.10 |
| Mass flow rate/kg/h | 1543 | 891 | 7 | 138 |
| Formaldehyde | — | — | 5.69E−06 | 6.35E−03 |
| Acetic acid | — | — | 7.51E−01 | 1.82E−03 |
| Acrylic acid | — | — | 7.40E−02 | 1.88E−06 |
| Water | — | — | 3.16E−03 | 4.38E−01 |
| Methanol | — | — | 1.55E−07 | 6.17E−02 |
| Formic acid | — | — | 3.71E−02 | 3.56E−10 |
| Propionic acid | — | — | 1.13E−05 | — |
| Acetone | — | — | 1.11E−10 | 1.90E−02 |
| Acetaldehyde | — | — | — | 5.78E−02 |
| Acrolein | — | — | 1.84E−11 | 4.25E−02 |
| Methyl acetate | — | — | 2.24E−11 | 2.18E−01 |
| Methyl acrylate | — | — | 6.91E−06 | 1.45E−01 |
| Methacrolein | — | — | 1.70E−07 | 1.44E−03 |
| Ethylene | — | — | — | 1.67E−03 |
| Carbon dioxide | — | 5.80E−04 | 7.84E−05 | 4.21E−06 |
| Oxygen | — | 2.31E−01 | 3.13E−02 | 1.68E−03 |
| Carbon monoxide | — | — | — | — |
| Nitrogen | 1.00E+00 | 7.68E−01 | 1.04E−01 | 5.57E−03 |

TABLE 6.1

Composition of the streams (in g/g of stream) at a molar ratio of acetic acid to formaldehyde in S3 of 4:1

| | Stream | | | | | |
|---|---|---|---|---|---|---|
| | S0 | S1 | S2 | S3 | S4 | S5 |
| State | L | L | L | G | G | G |
| Temperature/° C. | 20 | 53 | 20 | 302 | 370 | 0 |
| Pressure/bar | 1.00 | 1.50 | 1.00 | 1.40 | 1.10 | 1.00 |
| Mass flow rate/kg/h | 1102 | 2087 | 1075 | 12922 | 13029 | 3700 |
| Formaldehyde | 4.90E−01 | 5.66E−1 | — | 7.21E−02 | 3.15E−02 | 7.81E−05 |
| Acetic acid | — | 9.60E−02 | 9.80E−01 | 5.77E−01 | 4.94E−01 | 6.12E−03 |
| Acrylic acid | — | 1.27E−04 | — | 7.88E−03 | 8.47E−02 | 5.10E−04 |
| Water | 4.90E−01 | 3.34E−01 | 2.00E−02 | 7.40E−02 | 1.01E−01 | 1.81E−03 |
| Methanol | 2.00E−02 | 2.92E−03 | — | 1.71E−03 | 1.69E−03 | 2.92E−05 |
| Formic acid | 2.50E−04 | 1.40E−04 | — | 2.26E−05 | 2.24E−05 | 2.83E−07 |
| Propionic acid | — | 2.48E−11 | 4.00E−04 | 3.33E−05 | 3.30E−05 | 1.27E−07 |
| Acetone | — | 1.09E−11 | — | 2.02E−09 | 2.74E−04 | 7.07E−05 |
| Acetaldehyde | — | — | — | 2.35E−08 | 9.37E−04 | 8.21E−04 |
| Acrolein | — | — | — | 5.90E−09 | 5.74E−04 | 2.06E−04 |
| Methyl acetate | — | 3.53E−12 | — | 2.94E−08 | 2.91E−03 | 1.03E−03 |
| Methyl acrylate | — | — | — | 6.05E−09 | 1.71E−03 | 2.11E−04 |
| Methacrolein | — | 1.64E−09 | — | 3.75E−10 | 3.45E−05 | 3.86E−06 |
| Ethylene | — | — | — | 5.09E−08 | 5.25E−04 | 1.78E−03 |
| Carbon dioxide | — | — | — | 5.78E−05 | 1.05E−02 | 3.69E−02 |
| Oxygen | — | — | — | 2.26E−02 | 2.24E−02 | 7.90E−02 |
| Carbon monoxide | — | — | — | 4.94E−07 | 4.90E−03 | 1.72E−02 |
| Nitrogen | — | — | — | 2.45E−01 | 2.43E−01 | 8.54E−01 |

TABLE 6.2

Composition of the streams at a molar ratio of acetic acid to formaldehyde in S3 of 4:1

| | Stream | | | | | |
|---|---|---|---|---|---|---|
| | S6 | S7 | S8 | S9 | S10a | S11 |
| State | G | L | L | L | L | L |
| Temperature/° C. | 120 | 40 | 66 | 20 | 40 | 40 |
| Pressure/bar | 1.45 | 1.00 | 0.15 | 1.00 | 1.47 | 1.00 |
| Mass flow rate/kg/h | 9328 | 21022 | 14715 | 6307 | 13703 | 3333 |
| Formaldehyde | 4.39E−02 | — | — | — | — | — |
| Acetic acid | 6.88E−01 | 8.73E−01 | 8.26E−01 | 9.83E−01 | 8.86E−01 | 9.20E−03 |
| Acrylic acid | 1.18E−01 | 1.18E−01 | 1.61E−01 | 1.61E−02 | 1.00E−01 | 9.89E−01 |
| Water | 1.40E−01 | 6.20E−04 | 6.88E−04 | 4.61E−04 | 7.38E−04 | 6.15E−11 |
| Methanol | 2.35E−03 | 1.59E−08 | 2.27E−08 | — | 2.44E−08 | — |
| Formic acid | 3.11E−05 | 8.22E−03 | 1.17E−02 | — | 1.26E−02 | 2.68E−09 |
| Propionic acid | 4.61E−05 | 3.50E−05 | 5.00E−05 | — | 2.23E−05 | 1.37E−03 |
| Acetone | 3.55E−04 | 1.45E−10 | 2.08E−10 | — | 2.22E−10 | — |
| Acetaldehyde | 9.82E−04 | — | — | — | — | — |
| Acrolein | 7.20E−04 | 1.16E−10 | 1.66E−10 | — | 1.77E−10 | — |
| Methyl acetate | 3.65E−03 | 5.09E−11 | 7.28E−11 | — | 7.77E−11 | — |
| Methyl acrylate | 2.31E−03 | 1.04E−04 | 1.49E−04 | — | 1.59E−04 | 2.71E−11 |
| Methacrolein | 4.66E−05 | 3.89E−08 | 5.56E−08 | — | 5.95E−08 | — |
| Ethylene | 2.71E−05 | — | — | — | — | — |
| Carbon dioxide | — | — | — | — | — | — |
| Oxygen | — | — | — | — | — | — |
| Carbon monoxide | — | — | — | — | — | — |
| Nitrogen | — | — | — | — | — | — |

TABLE 6.3

Composition of the streams at a molar ratio of acetic acid to formaldehyde in S3 of 4:1

| | Stream | | | | | |
|---|---|---|---|---|---|---|
| | S12 | S13 | S14 | S15a | S16a | S17 |
| State | L | L | L | L | L | L |
| Temperature/° C. | 87 | 70 | 25 | 97 | 40 | 60 |
| Pressure/bar | 0.15 | 1.00 | 1.00 | 1.30 | 1.02 | 0.17 |
| Mass flow rate/kg/h | 2 | 2333 | 1000 | 2009 | 881 | 985 |
| Formaldehyde | — | — | — | 2.04E−01 | 3.66E−05 | 3.98E−01 |
| Acetic acid | 4.60E−03 | 1.23E−02 | 2.00E−03 | 1.00E−01 | 6.20E−04 | 2.03E−01 |
| Acrylic acid | 9.94E−01* | 9.86E−01 | 9.98E−01 | 1.32E−04 | 7.70E−08 | 2.70E−04 |
| Water | 1.24E−11 | 8.76E−11 | 6.15E−13 | 6.47E−01 | 9.49E−01 | 3.98E−01 |
| Methanol | — | — | — | 1.09E−02 | 1.27E−02 | 1.54E−05 |
| Formic acid | 6.47E−10 | 3.83E−09 | — | 8.00E−06 | 1.72E−06 | 1.63E−05 |
| Propionic acid | 1.40E−03 | 1.77E−03 | 4.27E−04 | 2.57E−11 | — | 5.25E−11 |
| Acetone | — | — | — | 1.65E−03 | 6.82E−04 | 2.31E−11 |
| Acetaldehyde | — | — | — | 4.56E−03 | 9.50E−04 | 3.40E−13 |
| Acrolein | — | — | — | 3.34E−03 | 6.28E−04 | 1.23E−12 |
| Methyl acetate | — | — | — | 1.70E−02 | 3.04E−03 | 7.48E−12 |
| Methyl acrylate | 5.69E−12 | 3.87E−11 | — | 1.07E−02 | 1.20E−03 | 3.45E−12 |
| Methacrolein | — | — | — | 2.17E−04 | 2.59E−04 | 3.47E−09 |
| Ethylene | — | — | — | 1.26E−04 | 1.39E−06 | — |
| Carbon dioxide | — | — | — | — | — | — |
| Oxygen | — | — | — | — | — | — |
| Carbon monoxide | — | — | — | — | — | — |
| Nitrogen | — | — | — | — | — | — |

*may also be present in the form of high-boiling acrylic acid adducts, for example dimer and/or oligomer.

TABLE 6.4

Composition of the streams at a molar ratio of acetic acid to formaldehyde in S3 of 4:1

| | Stream | | | |
|---|---|---|---|---|
| | S18 | S19 | S20 | S21 |
| State | G | G | G | G |
| Temperature/° C. | 20 | 20 | 40 | 40 |
| Pressure/bar | 1.50 | 1.50 | 0.06 | 0.10 |
| Mass flow rate/kg/h | 2190 | 1264 | 12 | 144 |
| Formaldehyde | — | — | — | 6.37E−03 |
| Acetic acid | — | — | 8.37E−01 | 1.09E−04 |

TABLE 6.4-continued

Composition of the streams at a molar ratio of acetic acid to formaldehyde in S3 of 4:1

| | Stream | | | |
|---|---|---|---|---|
| | S18 | S19 | S20 | S21 |
| Acrylic acid | — | — | 5.14E−02 | 1.10E−08 |
| Water | — | — | 1.10E−03 | 4.41E−01 |
| Methanol | — | — | 7.49E−08 | 6.18E−02 |
| Formic acid | — | — | 2.37E−02 | 2.31E−10 |
| Propionic acid | — | — | 9.01E−06 | — |
| Acetone | — | — | 1.41E−09 | 1.89E−02 |
| Acetaldehyde | — | — | — | 5.79E−02 |
| Acrolein | — | — | 1.33E−09 | 4.29E−02 |
| Methyl acetate | — | — | 5.78E−10 | 2.18E−01 |
| Methyl acrylate | — | — | 3.50E−04 | 1.42E−01 |
| Methacrolein | — | — | 2.31E−07 | 1.44E−03 |
| Ethylene | — | — | — | 1.75E−03 |
| Carbon dioxide | — | 5.80E−04 | 5.02E−05 | 4.04E−06 |
| Oxygen | — | 2.31E−01 | 2.00E−02 | 1.61E−03 |
| Carbon monoxide | — | — | — | — |
| Nitrogen | 1.00E+00 | 7.68E−01 | 6.64E−02 | 5.34E−03 |

LITERATURE CITED

Vitcha and Sims, I & EC Product Research and Development, vol. 5, no. 1, March 1966, pages 50 to 53
WO 2014/070735 A1

The invention claimed is:

1. A process for obtaining acrylic acid, comprising
   (a) providing a liquid stream S7 comprising acetic acid and acrylic acid, where the molar ratio of acetic acid to acrylic acid in stream S7 is greater than 1:1,
   (b-1) crystallizing a portion of the acetic acid present in stream S7 to obtain solid crystallized acetic acid in its mother liquor,
   (b-2) separating the mother liquor from the acetic acid crystallized in (b-1) to obtain the solid crystallized acetic acid and a liquid stream S8 comprising acrylic acid and acetic acid,
   (c) separating stream S8 into at least one stream S10 depleted of acrylic acid compared to S8 and a stream S11 enriched in acrylic acid compared to S8.

2. The process according to claim 1, wherein the molar ratio of acetic acid to acrylic acid in stream S7 is in the range from 1.1:1 to 20:1.

3. The process according to claim 1, wherein stream S7 consists of acetic acid and acrylic acid to an extent of 45% to 100% by weight.

4. The process according to claim 1, wherein stream S7 consists of acetic acid, acrylic acid, water, formaldehyde and any formic acid to an extent of 45% to 100% by weight.

5. The process according to claim 1, additionally comprising
   (b-3) optionally after one or more workup steps which follow on from (b-2), melting the solid crystallized acetic acid separated in (b-2), to obtain a stream S9.

6. The process according to claim 5, wherein the acetic acid content of stream S9 is from 80% to 99.999% by weight.

7. The process according to claim 5, wherein stream S9, optionally after one or more workups, is at least partly recycled into the process for obtaining acrylic acid.

8. The process according to claim 1, wherein the crystallizing in (b-1) is effected by means of layer crystallization on at least one heat exchanger surface.

9. The process according to claim 1, wherein the crystallizing in (b-1) is effected by means of suspension crystallization to obtain a suspension comprising solid crystallized acetic acid.

10. The process according to claim 9, wherein crystallization is accomplished by cooling at least a portion of stream S7 to an end temperature in the range from −35 to +17° C.

11. The process according to claim 1, wherein stream S7 originates from an aldol condensation.

12. The process according to claim 1, wherein the providing of the liquid stream S7 in (a) comprises:
   (a-1) providing a gaseous stream S3 comprising acetic acid, formaldehyde and optionally inert gas,
   (a-2) contacting stream S3 with an aldol condensation catalyst to obtain a stream S4 comprising acetic acid and acrylic acid,
   (a-3) optionally separating stream S4 to obtain a stream S5 comprising inert gas and a stream S6 comprising acetic acid and acrylic acid, or comprising acetic acid, acrylic acid, water, formaldehyde and any formic acid,
   (a-4) optionally separating stream S6 to obtain a stream S15 enriched in formaldehyde compared to S6 and a stream S7 depleted of formaldehyde compared to S6,
   where, if (a-3) is not conducted and (a-4) is conducted, S4 is the same as S6;
   where, if (a-4) is not conducted and (a-3) is conducted, S6 is the same as S7;
   where, if neither (a-3) nor (a-4) is conducted, S4 is the same as S7.

13. The process according to claim 12, comprising
   (b-3) optionally after one or more workup steps which follow on from (b-2), melting the solid crystallized acetic acid separated in (b-2), to obtain a stream S9,
   where stream S9 is at least partly recycled into (a-1).

14. The process according to claim 1, additionally comprising
   (d-1) crystallizing at least a portion of the acrylic acid present in S11 to obtain solid crystallized acrylic acid in its mother liquor.

15. The process according to claim 14, additionally comprising
   (d-2) separating the mother liquor from the acrylic acid crystallized in (d-1) to obtain the solid crystallized acrylic acid and a liquid stream S13.

16. The process according to claim 12, wherein stream S10 is at least partly recycled into the column in (a-4).

* * * * *